United States Patent
Cavalli et al.

(10) Patent No.: US 12,098,175 B2
(45) Date of Patent: Sep. 24, 2024

(54) PEPTIDE INHIBITORS TARGETING THE CXCL12/HMGB1 INTERACTION AND USES THEREOF

(71) Applicant: INSTITUTE FOR RESEARCH IN BIOMEDICINE, Bellinzona (CH)

(72) Inventors: Andrea Cavalli, Zurich (CH); Jacopo Sgrignani, Stezzano (IT); Mariagrazia Uguccioni, Bellinzona (CH)

(73) Assignee: INSTITUTE FOR RESEARCH IN BIOMEDICINE, Bellinzona (CH)

( * ) Notice: Subject to any disclaimer, the term of this patent is extended or adjusted under 35 U.S.C. 154(b) by 498 days.

(21) Appl. No.: 17/440,527

(22) PCT Filed: Mar. 20, 2020

(86) PCT No.: PCT/EP2020/057892
§ 371 (c)(1),
(2) Date: Sep. 17, 2021

(87) PCT Pub. No.: WO2020/188110
PCT Pub. Date: Sep. 24, 2020

(65) Prior Publication Data
US 2022/0153792 A1 May 19, 2022

(30) Foreign Application Priority Data
Mar. 21, 2019 (WO) .................. PCT/EP2019/057125

(51) Int. Cl.
*C07K 14/47* (2006.01)
*A61K 38/00* (2006.01)
*C07K 7/06* (2006.01)

(52) U.S. Cl.
CPC ............ *C07K 14/4703* (2013.01); *C07K 7/06* (2013.01); *A61K 38/00* (2013.01)

(58) Field of Classification Search
CPC ....... C07K 14/4703; C07K 7/06; A61K 38/00
See application file for complete search history.

(56) References Cited

U.S. PATENT DOCUMENTS

2014/0357512 A1   12/2014   Yang et al.

FOREIGN PATENT DOCUMENTS

| EP | 3004141 A1 | 4/2016 |
| WO | 2011119484 A1 | 9/2011 |
| WO | 2011133948 A2 | 10/2011 |
| WO | 2016172722 A1 | 10/2016 |
| WO | 2016187508 A2 | 11/2016 |

OTHER PUBLICATIONS

Nesprin-1 isoform X5 [Anoplophora glabripennis], from https://www.ncbi.nlm.nih.gov/protein/XP_018564400.1?report=genbank&log$=protalign&blast_rank=55&RID=ZGNFDDDH013, 2018, pp. 1-7.*
International Search Report from corresponding PCT Application No. PCT/EP2020/057892 dated Jul. 24, 2020.
Written Opinion from corresponding PCT Application No. PCT/EP2020/057892 dated Jul. 24, 2020.
Yang, H., et al., "Reversing established sepsis with antagonists of endogenous high-mobility group box 1," PNAS, 101 (1): 296-301 (2004).
Mollica, L., et al., "Glycyrrhizin Binds to High-Mobility Group Box 1 Protein and Inhibits Its Cytokine Activities," Chemistry & Biology, 14: 431-441 (2007).
Schiraldi, M., et al., "HMGB1 promotes recruitment of inflammatory cells to damaged tissues by forming a complex with CXCL 12 and signaling via CXCR4," J. Exp. Med., 209(3): 551-563 (2012).
Sgrignani, J., et al., "Systematic development of peptide inhibitors targeting the CXCL12/HMGB1 interaction," bioRxiv, p. 1-32 (2020).

* cited by examiner

*Primary Examiner* — Li N Komatsu
(74) *Attorney, Agent, or Firm* — Harness Dickey & Pierce P.L.C.

(57) ABSTRACT

The present invention provides novel peptides binding to HMGB1 and inhibiting the interaction of HMGB1 and CX-CL12. The present invention also provides proteins, virus-like particles, nanoparticles and compositions comprising such peptides and nucleic acids encoding such peptides. In addition, methods for using the peptides are provided. In particular, the peptides are useful in the treatment of inflammation and immune-related diseases.

21 Claims, 10 Drawing Sheets

Specification includes a Sequence Listing.

```
                9
MGKGDPKKPRGKMSSYAFFVQTCREEHKKKHPDASVNFSEFSKK
                                     79       88
CSERWKTMSAKEKGKFEDMAKADKARYEREMKTYIPPKGETKKK

FKDPNAPKRPPSAFFLFCSEYRPKIKGEHPGLSIGDVAKKLGEM
                   162
WNNTAADDKQPYEKKAAKLKEKYEKDIAAYRAKGKPDAAKKGVV
      186                                214
KAEKSKKKKEEEEDEEDEEDEEEEDEEDEDEEEDDDDE
```

HMGB1 BoxA amino acids 9-79
HMGB1 BoxB amino acids 88-162
HMGB1 acidic tail amino acids 186-214

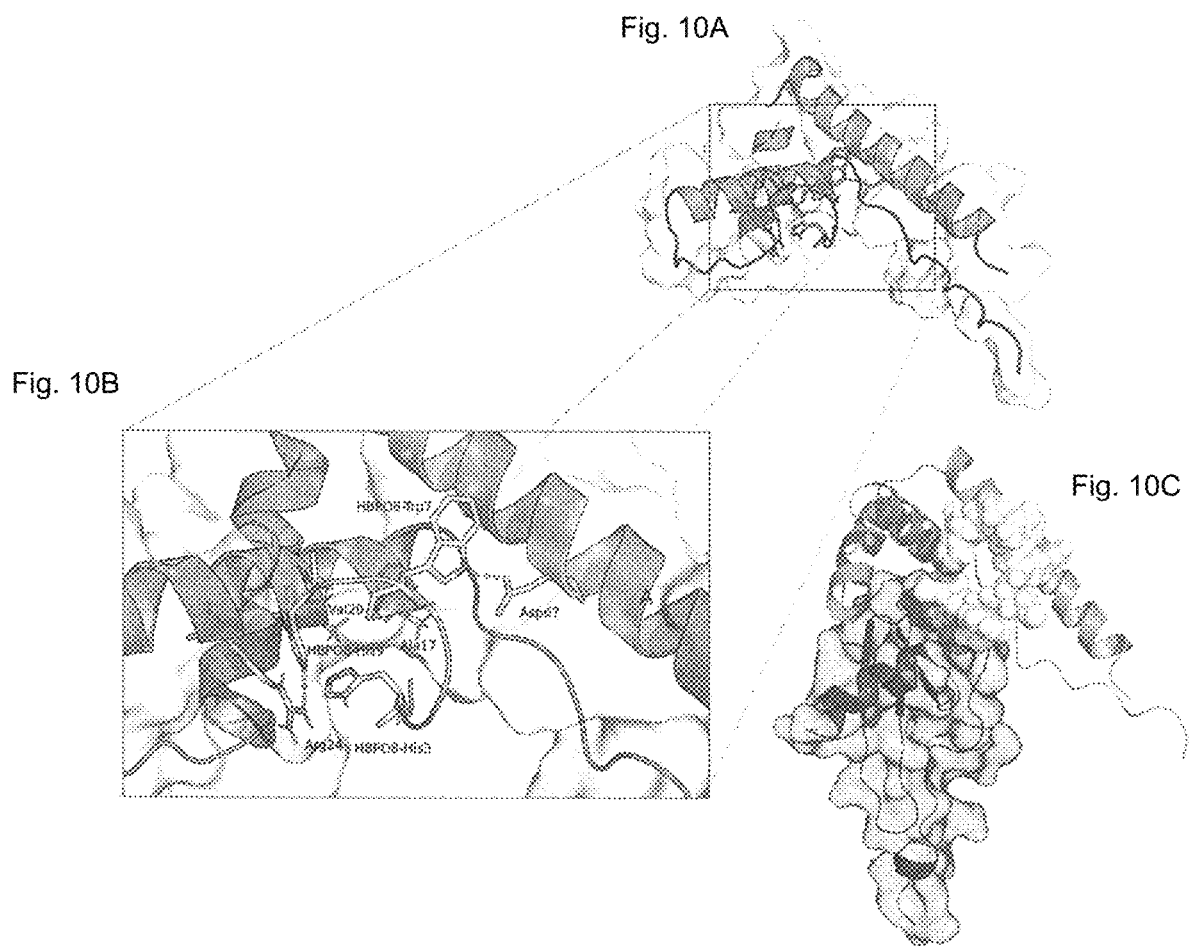

SEQUENCE LISTING

```
<160> NUMBER OF SEQ ID NOS: 74

<210> SEQ ID NO 1
<211> LENGTH: 9
<212> TYPE: PRT
<213> ORGANISM: Artificial Sequence
<220> FEATURE:
<223> OTHER INFORMATION: HBP08

<400> SEQUENCE: 1

Gly Tyr His Tyr Glu Arg Trp Ile His
1               5

<210> SEQ ID NO 2
<211> LENGTH: 9
<212> TYPE: PRT
<213> ORGANISM: Artificial Sequence
<220> FEATURE:
<223> OTHER INFORMATION: HBP07

<400> SEQUENCE: 2

His Trp Thr Leu Ala Asn Trp Cys Arg
1               5

<210> SEQ ID NO 3
<211> LENGTH: 9
<212> TYPE: PRT
<213> ORGANISM: Artificial Sequence
<220> FEATURE:
<223> OTHER INFORMATION: HBP05

<400> SEQUENCE: 3

Trp Ile Ser Asn Trp Ile Leu Met Trp
1               5

<210> SEQ ID NO 4
<211> LENGTH: 9
<212> TYPE: PRT
<213> ORGANISM: Artificial Sequence
<220> FEATURE:
<223> OTHER INFORMATION: HBP12

<400> SEQUENCE: 4
```

```
Tyr His Ile Cys Trp Tyr Gly Asp Tyr
1               5

<210> SEQ ID NO 5
<211> LENGTH: 9
<212> TYPE: PRT
<213> ORGANISM: Artificial Sequence
<220> FEATURE:
<223> OTHER INFORMATION: HBP01

<400> SEQUENCE: 5

His Glu Met Tyr Trp Glu Asp Glu Trp
1               5

<210> SEQ ID NO 6
<211> LENGTH: 9
<212> TYPE: PRT
<213> ORGANISM: Artificial Sequence
<220> FEATURE:
<223> OTHER INFORMATION: HBP02

<400> SEQUENCE: 6

Ile Asp Leu Arg Phe Phe Met Arg Gln
1               5

<210> SEQ ID NO 7
<211> LENGTH: 9
<212> TYPE: PRT
<213> ORGANISM: Artificial Sequence
<220> FEATURE:
<223> OTHER INFORMATION: HBP03

<400> SEQUENCE: 7

Phe Ala Phe Glu Leu Ile Gln Thr Asp
1               5

<210> SEQ ID NO 8
<211> LENGTH: 9
<212> TYPE: PRT
<213> ORGANISM: Artificial Sequence
<220> FEATURE:
<223> OTHER INFORMATION: HBP04

<400> SEQUENCE: 8

Cys Ile Pro Met Met Met His Ala Trp
1               5

<210> SEQ ID NO 9
<211> LENGTH: 9
<212> TYPE: PRT
<213> ORGANISM: Artificial Sequence
<220> FEATURE:
<223> OTHER INFORMATION: HBP06

<400> SEQUENCE: 9

Thr Trp Asn Ile His Phe Ala Asp His
1               5

<210> SEQ ID NO 10
<211> LENGTH: 9
<212> TYPE: PRT
<213> ORGANISM: Artificial Sequence
<220> FEATURE:
<223> OTHER INFORMATION: HBP09

<400> SEQUENCE: 10
```

Gln Phe Met Lys Asn Cys Glu Glu Met
1               5

<210> SEQ ID NO 11
<211> LENGTH: 9
<212> TYPE: PRT
<213> ORGANISM: Artificial Sequence
<220> FEATURE:
<223> OTHER INFORMATION: HBP10

<400> SEQUENCE: 11

Ser Ile Asn Trp His Met Tyr Val Asn
1               5

<210> SEQ ID NO 12
<211> LENGTH: 9
<212> TYPE: PRT
<213> ORGANISM: Artificial Sequence
<220> FEATURE:
<223> OTHER INFORMATION: HBP11

<400> SEQUENCE: 12

Met Tyr Arg Glu Asn Gln Pro Thr Arg
1               5

<210> SEQ ID NO 13
<211> LENGTH: 9
<212> TYPE: PRT
<213> ORGANISM: Artificial Sequence
<220> FEATURE:
<223> OTHER INFORMATION: HBP13

<400> SEQUENCE: 13

Trp Leu Trp Tyr Glu Trp Gly Trp Gln
1               5

<210> SEQ ID NO 14
<211> LENGTH: 9
<212> TYPE: PRT
<213> ORGANISM: Artificial Sequence
<220> FEATURE:
<223> OTHER INFORMATION: peptide

<400> SEQUENCE: 14

Asp Tyr Cys Trp Lys Ile Met Thr Gln
1               5

<210> SEQ ID NO 15
<211> LENGTH: 9
<212> TYPE: PRT
<213> ORGANISM: Artificial Sequence
<220> FEATURE:
<223> OTHER INFORMATION: peptide

<400> SEQUENCE: 15

Trp Cys His Phe Phe Phe Pro His Trp
1               5

<210> SEQ ID NO 16
<211> LENGTH: 9
<212> TYPE: PRT
<213> ORGANISM: Artificial Sequence
<220> FEATURE:
<223> OTHER INFORMATION: peptide

<400> SEQUENCE: 16

Met Lys Ser Ser Asp Cys Cys Leu Glu

```
<210> SEQ ID NO 17
<211> LENGTH: 9
<212> TYPE: PRT
<213> ORGANISM: Artificial Sequence
<220> FEATURE:
<223> OTHER INFORMATION: peptide

<400> SEQUENCE: 17

Glu Trp Phe Val Met Lys His Leu Asn
1               5

<210> SEQ ID NO 18
<211> LENGTH: 9
<212> TYPE: PRT
<213> ORGANISM: Artificial Sequence
<220> FEATURE:
<223> OTHER INFORMATION: peptide

<400> SEQUENCE: 18

Met Ile Arg Asp Gln Ile Leu His Asn
1               5

<210> SEQ ID NO 19
<211> LENGTH: 9
<212> TYPE: PRT
<213> ORGANISM: Artificial Sequence
<220> FEATURE:
<223> OTHER INFORMATION: peptide

<400> SEQUENCE: 19

Trp His Gln Leu Thr Glu His Trp Ile
1               5

<210> SEQ ID NO 20
<211> LENGTH: 9
<212> TYPE: PRT
<213> ORGANISM: Artificial Sequence
<220> FEATURE:
<223> OTHER INFORMATION: peptide

<400> SEQUENCE: 20

His Asp His Asp Phe Trp Ala Trp Tyr
1               5

<210> SEQ ID NO 21
<211> LENGTH: 9
<212> TYPE: PRT
<213> ORGANISM: Artificial Sequence
<220> FEATURE:
<223> OTHER INFORMATION: peptide

<400> SEQUENCE: 21

Trp Gln Trp His Gln Phe Gln Gly Arg
1               5

<210> SEQ ID NO 22
<211> LENGTH: 9
<212> TYPE: PRT
<213> ORGANISM: Artificial Sequence
<220> FEATURE:
<223> OTHER INFORMATION: peptide

<400> SEQUENCE: 22

Val Met Ala Ser Trp Gln His Gly Leu
1               5
```

```
<210> SEQ ID NO 23
<211> LENGTH: 9
<212> TYPE: PRT
<213> ORGANISM: Artificial Sequence
<220> FEATURE:
<223> OTHER INFORMATION: peptide

<400> SEQUENCE: 23

Leu Asp Asn Phe Leu Gly Asp His Trp
1               5

<210> SEQ ID NO 24
<211> LENGTH: 9
<212> TYPE: PRT
<213> ORGANISM: Artificial Sequence
<220> FEATURE:
<223> OTHER INFORMATION: peptide

<400> SEQUENCE: 24

Pro Arg Met Gly Trp Glu Lys Pro Glu
1               5

<210> SEQ ID NO 25
<211> LENGTH: 9
<212> TYPE: PRT
<213> ORGANISM: Artificial Sequence
<220> FEATURE:
<223> OTHER INFORMATION: peptide

<400> SEQUENCE: 25

Trp Ile Cys Val Trp His His Ala Ser
1               5

<210> SEQ ID NO 26
<211> LENGTH: 9
<212> TYPE: PRT
<213> ORGANISM: Artificial Sequence
<220> FEATURE:
<223> OTHER INFORMATION: peptide

<400> SEQUENCE: 26

Ile Arg Trp Cys Val Asp Ala Arg Tyr
1               5

<210> SEQ ID NO 27
<211> LENGTH: 9
<212> TYPE: PRT
<213> ORGANISM: Artificial Sequence
<220> FEATURE:
<223> OTHER INFORMATION: peptide

<400> SEQUENCE: 27

Trp Asn Ala Met Ser Phe Cys Cys Ser
1               5

<210> SEQ ID NO 28
<211> LENGTH: 9
<212> TYPE: PRT
<213> ORGANISM: Artificial Sequence
<220> FEATURE:
<223> OTHER INFORMATION: peptide

<400> SEQUENCE: 28

Ile Phe His Ile Met Thr Glu Met Trp
1               5
```

```
<210> SEQ ID NO 29
<211> LENGTH: 9
<212> TYPE: PRT
<213> ORGANISM: Artificial Sequence
<220> FEATURE:
<223> OTHER INFORMATION: peptide

<400> SEQUENCE: 29

Phe Asp Arg Pro Arg Tyr Arg Thr Thr
1               5

<210> SEQ ID NO 30
<211> LENGTH: 9
<212> TYPE: PRT
<213> ORGANISM: Artificial Sequence
<220> FEATURE:
<223> OTHER INFORMATION: peptide

<400> SEQUENCE: 30

Gln Ile Glu Asp Met Pro Thr Ser Lys
1               5

<210> SEQ ID NO 31
<211> LENGTH: 9
<212> TYPE: PRT
<213> ORGANISM: Artificial Sequence
<220> FEATURE:
<223> OTHER INFORMATION: peptide

<400> SEQUENCE: 31

Phe Asp Cys Met Met Asp Met Thr Lys
1               5

<210> SEQ ID NO 32
<211> LENGTH: 9
<212> TYPE: PRT
<213> ORGANISM: Artificial Sequence
<220> FEATURE:
<223> OTHER INFORMATION: peptide

<400> SEQUENCE: 32

Asn Thr Val Ala Leu Lys Leu Arg Asp
1               5

<210> SEQ ID NO 33
<211> LENGTH: 9
<212> TYPE: PRT
<213> ORGANISM: Artificial Sequence
<220> FEATURE:
<223> OTHER INFORMATION: peptide

<400> SEQUENCE: 33

Tyr His Tyr His Met Leu Met Gln Ser
1               5

<210> SEQ ID NO 34
<211> LENGTH: 9
<212> TYPE: PRT
<213> ORGANISM: Artificial Sequence
<220> FEATURE:
<223> OTHER INFORMATION: peptide

<400> SEQUENCE: 34

Asn Ile Thr His Asn Val Trp His Arg
1               5
```

```
<210> SEQ ID NO 35
<211> LENGTH: 9
<212> TYPE: PRT
<213> ORGANISM: Artificial Sequence
<220> FEATURE:
<223> OTHER INFORMATION: peptide

<400> SEQUENCE: 35

Asp Arg Asn Leu Glu Val Glu Gln Ile
1               5

<210> SEQ ID NO 36
<211> LENGTH: 9
<212> TYPE: PRT
<213> ORGANISM: Artificial Sequence
<220> FEATURE:
<223> OTHER INFORMATION: peptide

<400> SEQUENCE: 36

His Tyr Asn Lys Trp Lys His Gln Glu
1               5

<210> SEQ ID NO 37
<211> LENGTH: 9
<212> TYPE: PRT
<213> ORGANISM: Artificial Sequence
<220> FEATURE:
<223> OTHER INFORMATION: peptide

<400> SEQUENCE: 37

Ile Cys Met Pro Pro Asn Thr Lys Asn
1               5

<210> SEQ ID NO 38
<211> LENGTH: 9
<212> TYPE: PRT
<213> ORGANISM: Artificial Sequence
<220> FEATURE:
<223> OTHER INFORMATION: peptide

<400> SEQUENCE: 38

Ser Met Ile Pro Val Gln Glu Ala Ser
1               5

<210> SEQ ID NO 39
<211> LENGTH: 9
<212> TYPE: PRT
<213> ORGANISM: Artificial Sequence
<220> FEATURE:
<223> OTHER INFORMATION: peptide

<400> SEQUENCE: 39

Tyr Gln Arg Asn Glu Leu Glu Tyr Leu
1               5

<210> SEQ ID NO 40
<211> LENGTH: 9
<212> TYPE: PRT
<213> ORGANISM: Artificial Sequence
<220> FEATURE:
<223> OTHER INFORMATION: peptide

<400> SEQUENCE: 40

His Tyr Phe Asp Met Leu His Phe His
1               5

<210> SEQ ID NO 41
```

```
<211> LENGTH: 9
<212> TYPE: PRT
<213> ORGANISM: Artificial Sequence
<220> FEATURE:
<223> OTHER INFORMATION: peptide

<400> SEQUENCE: 41

Ser His Tyr Phe Lys His Ser Asn Phe
1               5

<210> SEQ ID NO 42
<211> LENGTH: 9
<212> TYPE: PRT
<213> ORGANISM: Artificial Sequence
<220> FEATURE:
<223> OTHER INFORMATION: peptide

<400> SEQUENCE: 42

Phe Ile Lys Gln Met Glu Glu Ser Thr
1               5

<210> SEQ ID NO 43
<211> LENGTH: 9
<212> TYPE: PRT
<213> ORGANISM: Artificial Sequence
<220> FEATURE:
<223> OTHER INFORMATION: peptide

<400> SEQUENCE: 43

Lys Tyr Gln Trp Met His Tyr Thr Pro
1               5

<210> SEQ ID NO 44
<211> LENGTH: 9
<212> TYPE: PRT
<213> ORGANISM: Artificial Sequence
<220> FEATURE:
<223> OTHER INFORMATION: HBP08-RI
<220> FEATURE:
<221> NAME/KEY: MISC_FEATURE
<222> LOCATION: (1)..(9)
<223> OTHER INFORMATION: all D-amino acids

<400> SEQUENCE: 44

His Ile Trp Arg Glu Tyr His Tyr Gly
1               5

<210> SEQ ID NO 45
<211> LENGTH: 9
<212> TYPE: PRT
<213> ORGANISM: Artificial Sequence
<220> FEATURE:
<223> OTHER INFORMATION: HBP08-A1

<400> SEQUENCE: 45

Ala Tyr His Tyr Glu Arg Trp Ile His
1               5

<210> SEQ ID NO 46
<211> LENGTH: 9
<212> TYPE: PRT
<213> ORGANISM: Artificial Sequence
<220> FEATURE:
<223> OTHER INFORMATION: HBP08-A2

<400> SEQUENCE: 46

Gly Ala His Tyr Glu Arg Trp Ile His
1               5
```

```
<210> SEQ ID NO 47
<211> LENGTH: 9
<212> TYPE: PRT
<213> ORGANISM: Artificial Sequence
<220> FEATURE:
<223> OTHER INFORMATION: HBP08-A3

<400> SEQUENCE: 47

Gly Tyr Ala Tyr Glu Arg Trp Ile His
1               5

<210> SEQ ID NO 48
<211> LENGTH: 9
<212> TYPE: PRT
<213> ORGANISM: Artificial Sequence
<220> FEATURE:
<223> OTHER INFORMATION: HBP08-A4

<400> SEQUENCE: 48

Gly Tyr His Ala Glu Arg Trp Ile His
1               5

<210> SEQ ID NO 49
<211> LENGTH: 9
<212> TYPE: PRT
<213> ORGANISM: Artificial Sequence
<220> FEATURE:
<223> OTHER INFORMATION: HBP08-A5

<400> SEQUENCE: 49

Gly Tyr His Tyr Ala Arg Trp Ile His
1               5

<210> SEQ ID NO 50
<211> LENGTH: 9
<212> TYPE: PRT
<213> ORGANISM: Artificial Sequence
<220> FEATURE:
<223> OTHER INFORMATION: HBP08-A6

<400> SEQUENCE: 50

Gly Tyr His Tyr Glu Ala Trp Ile His
1               5

<210> SEQ ID NO 51
<211> LENGTH: 9
<212> TYPE: PRT
<213> ORGANISM: Artificial Sequence
<220> FEATURE:
<223> OTHER INFORMATION: HBP08-A7

<400> SEQUENCE: 51

Gly Tyr His Tyr Glu Arg Ala Ile His
1               5

<210> SEQ ID NO 52
<211> LENGTH: 9
<212> TYPE: PRT
<213> ORGANISM: Artificial Sequence
<220> FEATURE:
<223> OTHER INFORMATION: HBP08-A8

<400> SEQUENCE: 52

Gly Tyr His Tyr Glu Arg Trp Ala His
1               5
```

```
<210> SEQ ID NO 53
<211> LENGTH: 9
<212> TYPE: PRT
<213> ORGANISM: Artificial Sequence
<220> FEATURE:
<223> OTHER INFORMATION: HBP08-A9

<400> SEQUENCE: 53

Gly Tyr His Tyr Glu Arg Trp Ile Ala
1               5

<210> SEQ ID NO 54
<211> LENGTH: 9
<212> TYPE: PRT
<213> ORGANISM: Artificial Sequence
<220> FEATURE:
<223> OTHER INFORMATION: HBP08-D2

<400> SEQUENCE: 54

Gly Asp His Tyr Glu Arg Trp Ile His
1               5

<210> SEQ ID NO 55
<211> LENGTH: 9
<212> TYPE: PRT
<213> ORGANISM: Artificial Sequence
<220> FEATURE:
<223> OTHER INFORMATION: HBP08-K9

<400> SEQUENCE: 55

Gly Tyr His Tyr Glu Arg Trp Ile Lys
1               5

<210> SEQ ID NO 56
<211> LENGTH: 9
<212> TYPE: PRT
<213> ORGANISM: Artificial Sequence
<220> FEATURE:
<223> OTHER INFORMATION: HBP08-K2

<400> SEQUENCE: 56

Gly Lys His Tyr Glu Arg Trp Ile His
1               5

<210> SEQ ID NO 57
<211> LENGTH: 9
<212> TYPE: PRT
<213> ORGANISM: Artificial Sequence
<220> FEATURE:
<223> OTHER INFORMATION: XHBP08

<400> SEQUENCE: 57

His Tyr Trp Tyr Glu Arg Trp Glu His
1               5

<210> SEQ ID NO 58
<211> LENGTH: 5
<212> TYPE: PRT
<213> ORGANISM: Artificial Sequence
<220> FEATURE:
<223> OTHER INFORMATION: Pentapept-2

<400> SEQUENCE: 58

Glu Arg Trp Ile His
1               5
```

<210> SEQ ID NO 59
<211> LENGTH: 5
<212> TYPE: PRT
<213> ORGANISM: Artificial Sequence
<220> FEATURE:
<223> OTHER INFORMATION: Pentapept-1

<400> SEQUENCE: 59

Gly Tyr His Tyr Glu
1               5

<210> SEQ ID NO 60
<211> LENGTH: 215
<212> TYPE: PRT
<213> ORGANISM: Homo sapiens

<400> SEQUENCE: 60

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Asp Glu Glu Asp Glu
        195                 200                 205

Glu Glu Asp Asp Asp Asp Glu
    210                 215

<210> SEQ ID NO 61
<211> LENGTH: 9
<212> TYPE: PRT
<213> ORGANISM: Artificial Sequence
<220> FEATURE:
<223> OTHER INFORMATION: peptide

<400> SEQUENCE: 61

Phe Val Gly Met Arg Trp Lys Phe Leu
1               5

<210> SEQ ID NO 62
<211> LENGTH: 9
<212> TYPE: PRT

```
<213> ORGANISM: Artificial Sequence
<220> FEATURE:
<223> OTHER INFORMATION: peptide

<400> SEQUENCE: 62

Trp Gln Ile Pro Asp His Arg Asp His
1               5

<210> SEQ ID NO 63
<211> LENGTH: 9
<212> TYPE: PRT
<213> ORGANISM: Artificial Sequence
<220> FEATURE:
<223> OTHER INFORMATION: peptide

<400> SEQUENCE: 63

Gln Cys Phe His Pro Ser Phe Glu Asp
1               5

<210> SEQ ID NO 64
<211> LENGTH: 9
<212> TYPE: PRT
<213> ORGANISM: Artificial Sequence
<220> FEATURE:
<223> OTHER INFORMATION: peptide

<400> SEQUENCE: 64

Val Pro Ser Ser Ala Lys Asn Arg Asp
1               5

<210> SEQ ID NO 65
<211> LENGTH: 9
<212> TYPE: PRT
<213> ORGANISM: Artificial Sequence
<220> FEATURE:
<223> OTHER INFORMATION: peptide

<400> SEQUENCE: 65

Lys His Met Thr Lys Cys Glu Gln Trp
1               5

<210> SEQ ID NO 66
<211> LENGTH: 9
<212> TYPE: PRT
<213> ORGANISM: Artificial Sequence
<220> FEATURE:
<223> OTHER INFORMATION: peptide

<400> SEQUENCE: 66

Glu Thr Tyr Gln Phe Arg Pro Asn Lys
1               5

<210> SEQ ID NO 67
<211> LENGTH: 9
<212> TYPE: PRT
<213> ORGANISM: Artificial Sequence
<220> FEATURE:
<223> OTHER INFORMATION: peptide

<400> SEQUENCE: 67

Trp Asn Cys His Arg Asp Arg Pro Lys
1               5

<210> SEQ ID NO 68
<211> LENGTH: 9
<212> TYPE: PRT
<213> ORGANISM: Artificial Sequence
```

```
<220> FEATURE:
<223> OTHER INFORMATION: peptide

<400> SEQUENCE: 68

Lys His Met Thr Lys Cys Glu Gln Trp
1               5

<210> SEQ ID NO 69
<211> LENGTH: 9
<212> TYPE: PRT
<213> ORGANISM: Artificial Sequence
<220> FEATURE:
<223> OTHER INFORMATION: peptide

<400> SEQUENCE: 69

Lys Cys Val Val Phe His Tyr Asp Pro
1               5

<210> SEQ ID NO 70
<211> LENGTH: 9
<212> TYPE: PRT
<213> ORGANISM: Artificial Sequence
<220> FEATURE:
<223> OTHER INFORMATION: peptide

<400> SEQUENCE: 70

Pro Thr Phe Glu Glu Phe Ala Ala Phe
1               5

<210> SEQ ID NO 71
<211> LENGTH: 9
<212> TYPE: PRT
<213> ORGANISM: Artificial Sequence
<220> FEATURE:
<223> OTHER INFORMATION: peptide

<400> SEQUENCE: 71

Gln Cys Phe His Pro Ser Phe Glu Asp
1               5

<210> SEQ ID NO 72
<211> LENGTH: 9
<212> TYPE: PRT
<213> ORGANISM: Artificial Sequence
<220> FEATURE:
<223> OTHER INFORMATION: peptide

<400> SEQUENCE: 72

Glu Trp Leu Tyr Arg Gln Glu Tyr His
1               5

<210> SEQ ID NO 73
<211> LENGTH: 9
<212> TYPE: PRT
<213> ORGANISM: Artificial Sequence
<220> FEATURE:
<223> OTHER INFORMATION: peptide

<400> SEQUENCE: 73

Gln Asp Tyr Ala Pro Arg Ala Ser Asn
1               5
```

```
<210> SEQ ID NO 74
<211> LENGTH: 9
<212> TYPE: PRT
<213> ORGANISM: Artificial Sequence
<220> FEATURE:
<223> OTHER INFORMATION: peptide

<400> SEQUENCE: 74

Lys Asp Lys Ala Phe Lys Asn Val Ser
1               5
```

PEPTIDE INHIBITORS TARGETING THE CXCL12/HMGB1 INTERACTION AND USES THEREOF

CROSS REFERENCE TO RELATED APPLICATIONS

This application is a 35 U.S.C § 371 National Stage Entry of International Patent Application No. PCT/EP2020/057892 filed 20 Mar. 2020, which claims foreign priority to International Patent Application No. PCT/EP2019/057125 filed 21 Mar. 2019, which are incorporated herein by reference in their entireties.

REFERENCE TO A SEQUENCE LISTING

This application contains references to nucleic acid and/or amino acid sequences as an ASC II text file. The name of the ASC II text file is "62901145_1.TXT". It was created on 23 Aug. 2021 and is 15 KB. The aforementioned sequence listing is hereby incorporated by reference in its entirety pursuant to 37 C.F.R. § 1.52(e).

FIELD

The present invention relates to the field of inhibitors of the CXCL12/HMGB1 interaction. In particular, the present invention provides novel peptides binding to HMGB1 and inhibiting the interaction of HMGB1 and CXCL12. The present invention also provides proteins, virus-like particles, nanoparticles and compositions comprising such peptides and nucleic acids encoding such peptides. In addition, methods for using the peptides are provided. In particular, the peptides are useful in the treatment of inflammation or immune-related diseases.

BACKGROUND

During inflammatory reactions, the production and release of chemotactic factors guide the recruitment of selective leukocyte subpopulations. High-Mobility-Group-Protein 1 (HMGB1) and the chemokine "CXC-Motiv-Chemokin 12" (CXCL12), both released in the microenvironment, form a heterocomplex, which exclusively acts on the chemokine receptor CXCR4, thereby enhancing monocyte migration and exacerbating the immune response.

Chemokines are key regulators of leukocyte migration and play fundamental roles both in physiological and pathological immune responses. Chemokine receptors differentially expressed by all leukocytes and many non-hematopoietic cells, including cancer cells, constitute the largest branch of the γ subfamily of rhodopsin-like G protein-coupled receptors (GPCR). In modern pharmacology, this receptor superfamily represents the most successful target of small molecule inhibitors for the treatment of diseases of a variety of organs and systems. In the last 25/30 years, an2mpressivee amount of preclinical and clinical evidence has progressively validated the role of chemokines and their receptors in immune-mediated diseases. The research of molecules inhibiting the interaction between chemokines and molecules able to enhance the chemokine activity is nowadays fundamental for the discovery of effective inhibitors of the chemokine system.

In the last decade, several studies have pointed out how cell migration induced by chemokines, can be further modulated by forming heterocomplexes with other chemokines or proteins released in inflammation (Cecchinato, V., D'Agostino, G., Raeli, L. & Uguccioni, M. Chemokine interaction with synergy-inducing molecules: fine tuning modulation of cell trafficking. *J Leukoc Biol* 99, 851-5 (2016)). In particular, it was shown that HMGB1, an alarmin released under stress conditions, forms a heterocomplex with the chemokine CXCL12, enhancing cell migration via the chemokine receptor cxcr4 both in vitro and in in vivo (Schiraldi, M. et al. HMGB1 promotes recruitment of inflammatory cells to damaged tissues by forming a complex with CXCL12 and signaling via CXCR4. *J Exp Med* 209, 551-63 (2012); Proudfoot, A. E. & Uguccioni, M. Modulation of Chemokine Responses: Synergy and Cooperativity. *Front Immunol* 7, 183 (2016)).

HMGB1 is a highly conserved nuclear protein expressed in bacteria, yeast, plants and in all vertebrate cells. Structurally, it is composed of two homologous, but not identical domains, BoxA and BoxB, and a negatively charged C-terminal tail (FIG. 1; Lotze, M. T. & Tracey, K. J. High-mobility group box 1 protein (HMGB1): nuclear weapon in the immune arsenal. *Nat Rev Immunol* 5, 331-42 (2005); Stott, K., Watson, M., Howe, F. S., Grossmann, J. G. & Thomas, J. O. Tail-mediated collapse of HMGB1 is dynamic and occurs via differential binding of the acidic tail to the A and B domains. *J Mol Biol* 403, 706-22 (2010)). In addition to its nuclear function, HMGB1 can be released by necrotic cells or under inflammatory conditions and act as a damage-associated molecular pattern molecule (DAMP) (Andersson, U. & Tracey, K. J. HMGB1 is a therapeutic target for sterile inflammation and infection. *Annu Rev Immunol* 29, 139-62 (2011)).

In the extracellular space, HMGB1 can be present in two mutually exclusive redox states, depending on the presence of a reversible intramolecular disulfide bond between two cysteines at position 23 and 45 (Venereau, E. et al. Mutually exclusive redox forms of HMGB1 promote cell recruitment or proinflammatory cytokine release. *J Exp Med* 209, 1519-28 (2012)). Reduced HMGB1, once released in the extracellular space, can form a heterocomplex with CXCL12 and synergistically promote, via CXCR4, the recruitment of monocytes to inflammatory sites (Schiraldi, M. et al. HMGB1 promotes recruitment of inflammatory cells to damaged tissues by forming a complex with CXCL12 and signaling via CXCR4. *J Exp Med* 209, 551-63 (2012)). Once oxidized, by the presence of reactive oxidative species in the extracellular space, HMGB1 binds to the Toll-like Receptor 4 (TLR4) and RAGE, leading to activation of the nuclear factor kappa-B (NK-Kb) and the transcription of cytokines (Venereau, E. et al. Mutually exclusive redox forms of HMGB1 promote cell recruitment or proinflammatory cytokine release. *J Exp Med* 209, 1519-28 (2012); Yang, H. et al. MD-2 is required for disulfide HMGB1-dependent TLR4 signaling. *J Exp Med* 212, 5-14 (2015)).

An excessive cell influx at the inflammatory site can result in excessive inflammation and excessive immune responses. However, despite the importance of this target, only few inhibitors of the CXCL12/HMGB1 interaction have been identified so far, such as glycyrrhizin (Mollica, L. et al. Glycyrrhizin binds to high-mobility group box 1 protein and inhibits its cytokine activities. *Chem Biol* 14, 431-41 (2007); Choi, H. W. et al. Aspirin's Active Metabolite Salicylic Acid Targets High Mobility Group Box 1 to Modulate Inflammatory Responses. *Mol Med* 21, 526-35 (2015)).

SUMMARY

In view of the above, it is the object of the present invention to provide novel inhibitors of the CXCL12/

HMGB1 interaction. In particular, it is an object of the present invention to provide peptide inhibitors of the CXCL12/HMGB1 interaction.

This object is achieved by means of the subject-matter set out below and in the appended claims.

BRIEF DESCRIPTION OF THE FIGURES

In the following a brief description of the appended figures will be given. The figures are intended to illustrate the present invention in more detail. However, they are not intended to limit the subject matter of the invention in any way.

FIG. 10A-10C shows a molecular model of the HBP08-BoxA complex (FIG. 10A), with an enlargement (FIG. 10B) of the specific critical interactions of HBP08 and BoxA of HMGB1. Binding of HBP08 with respect to the structure of BoxA-CXCL12 complex obtained by docking is shown in (FIG. 10C).

DETAILED DESCRIPTION

Figures 1A, 1B:
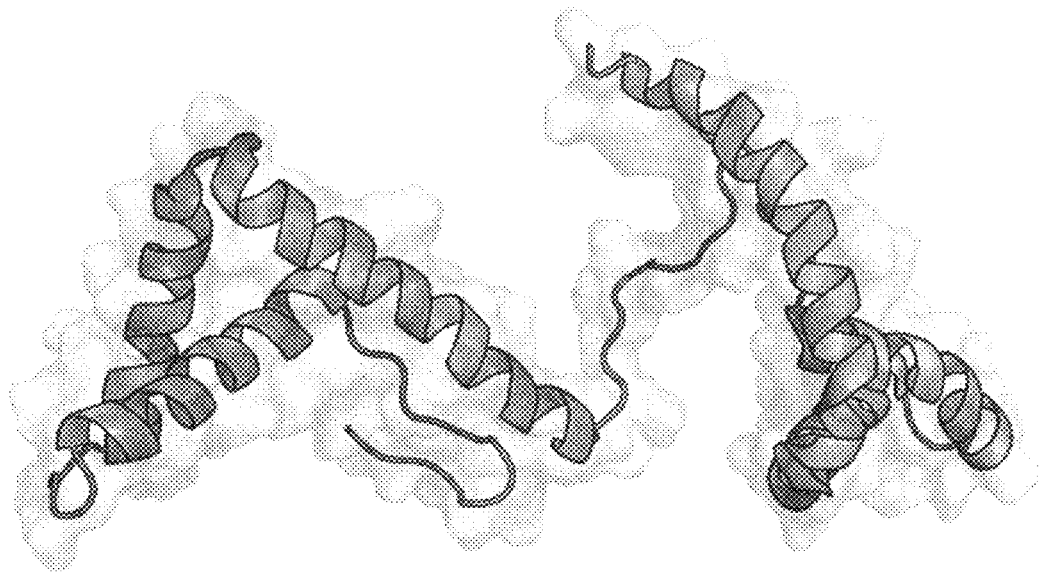
FIG. 1A-1B shows a linear representation of high-mobility protein box 1 (HMGB1; SEQ ID NO: 60), including residues that constitute the BoxA, BoxB and their acidic tail (FIG. 1A). In addition, ribbon representation of the solution structure of HMGB1 fragment 2-174 (PDB 2YRQ) is shown (FIG. 1B).

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

As used herein, the terms "peptide", "polypeptide", and "protein" and variations of these terms typically refer to a molecule, in particular a peptide, an oligopeptide, a polypeptide or a protein, such as a fusion protein, comprising at least two amino acids joined to each other by a normal peptide bond, or by a modified peptide bond, such as for example in the cases of isosteric peptides.

For example, a "classical" peptide, polypeptide or protein is typically composed of amino acids selected from the 20 amino acids defined by the genetic code, linked to each other by a normal peptide bond. A peptide, polypeptide or protein can be composed of L-amino acids and/or D-amino acids. Preferably, a peptide, polypeptide or protein is either (entirely) composed of L-amino acids or (entirely) of D-amino acids.

In particular, the terms "peptide", "polypeptide", "protein" also include "peptidomimetics". Peptidomimetics are defined as modified peptides, wherein the modification does not occur in nature. Examples of modifications include altered backbones, the incorporation of nonnatural amino acids and other non-peptidic structural elements. Peptidomimetics are typically capable of mimicking or antagonizing the biological action(s) of a natural parent peptide. For example, a peptidomimetic may lack classical peptide characteristics such as enzymatically scissile peptide bonds. Typically, peptidomimetics arise either from modification of an existing peptide, or by designing similar systems that mimic peptides, such as peptoids and β-peptides. The peptide according to the present invention may be a D-retro-inverso version of an L-peptide. In general, D-retro-inverso-peptides are known in the art (Guichard G, Benkirane N, Zeder-Lutz G, van Regenmortel M H, Briand J P, Muller S (1994). Antigenic mimicry of natural L-peptides with retro-inverso-peptidomimetics. Proceedings of the National Academy of Sciences. 91 (21): 9765-9769). D-retro-inverso-peptides are D-peptides in the reversed sequence, such that side chain positions are very similar to those of the "parent" L-peptide. D-peptides are less susceptible to be degraded in the stomach or inside cells by proteolysis, and, thus, not easily digested or degraded. D-retro inverso peptides are typically designed to mimic a "parent" L-peptide.

A peptide, polypeptide or protein may comprise amino acids other than the 20 amino acids defined by the genetic code in addition to these amino acids, or it may be composed of amino acids other than the 20 amino acids defined by the genetic code. In particular, a peptide, polypeptide or protein can equally be composed of amino acids modified by natural processes, such as post-translational maturation processes or by chemical processes, which are well known to a person skilled in the art. Such modifications are fully detailed in the literature. These modifications can appear anywhere in the polypeptide: in the peptide skeleton, in the amino acid chain or even at the carboxy- or amino-terminal ends. In particular, a peptide, polypeptide or protein can be linear or branched. For example, a peptide, polypeptide or protein may be branched following an ubiquitination or be cyclic with or without branching. This type of modification can be the result of natural or synthetic post-translational processes that are well known to a person skilled in the art.

The terms "peptide", "polypeptide", "protein" in the context of the present invention in particular also include modified peptides, polypeptides and proteins. For example, peptide, polypeptide or protein modifications can include acetylation, acylation, ADP-ribosylation, amidation, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, glycosylation including pegylation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature (Proteins Structure and Molecular Properties (1993) 2nd Ed., T. E. Creighton, New York; Post-translational Covalent Modifications of Proteins (1983) B. C. Johnson, Ed., Academic Press, New York; Seifter et al. (1990) Analysis for protein modifications and nonprotein cofactors, Meth. Enzymol. 182: 626-646 and Rattan et al., (1992) Protein Synthesis: Post-translational Modifications and Aging, Ann NY Acad Sci, 663: 48-62). Accordingly, the terms "peptide", "polypeptide", "protein" preferably include, for example, lipopeptides, lipoproteins, glycopeptides, glycoproteins and the like.

In particular, a "peptide" or "polypeptide" comprises a single chain of amino acid monomers linked by peptide bonds. A "protein", as used herein, comprises one or more, e.g. 1, 2, 3, 4, 5, 6, 7, 8, 9 or 10 (poly)peptides, i.e. one or more chains of amino acid monomers linked by peptide bonds as explained above. Preferably, a protein according to the present invention comprises 1, 2, 3, or 4 polypeptides.

A peptide, polypeptide or protein may occur in nature or a peptide, polypeptide or protein may be recombinant. The term "recombinant", as used herein, refers to any peptide, polypeptide or protein which is prepared, expressed, created or isolated by recombinant means, and which is in particular not occurring in nature.

As used throughout this specification and the claims which follow, unless the context requires otherwise, the term "sequence variant" refers to any alteration in a reference sequence, whereby a reference sequence is any of the sequences listed in the "Table of Sequences and SEQ ID Numbers" (sequence listing), i.e. SEQ ID NO: 1 to SEQ ID NO: 74. Thus, the term "sequence variant" includes nucleotide sequence variants and amino acid sequence variants. In particular, in a "sequence variant" the functionality (of the reference sequence) is preserved, i.e. the sequence variant is functional (also referred to as "functional sequence variant"). A "sequence variant" as used herein typically has a sequence which is at least 75% identical to the reference sequence. Preferably, a sequence variant has a sequence which is at least 88% identical to the reference sequence.

Sequence identity is usually calculated with regard to the full length of the reference sequence (i.e. the sequence recited in the application). Percentage identity, as referred to herein, can be determined, for example, using BLAST using the default parameters specified by the NCBI (the National Center for Biotechnology Information; www.ncbi.nlm.nih.gov/) [Blosum 62 matrix; gap open penalty=11 and gap extension penalty=1].

A "sequence variant" in the context of a nucleotide sequence has an altered sequence in which one or more of the nucleotides in the reference sequence is deleted, or substituted, or one or more nucleotides are inserted into the sequence of the reference nucleotide sequence. Nucleotides are referred to herein by the standard one-letter designation (A, C, G, or T). Due to the degeneracy of the genetic code, a "sequence variant" of a nucleic acid (nucleotide) sequence can either result in a change in the respective reference amino acid sequence, i.e. in a "sequence variant" of the respective amino acid sequence or not. Preferred sequence variants are such nucleotide sequence variants, which do not result in amino acid sequence variants (silent mutations), but other non-silent mutations are within the scope as well, in particular mutant nucleotide sequences, which result in an amino acid sequence, which is at least 70% identical to the reference sequence, preferably at least 80% identical to the reference sequence, more preferably at least 90% identical, even more preferably at least 95% identical, and particularly preferably at least 99% identical to the reference sequence.

A "sequence variant" in the context of an amino acid has an altered sequence in which one or more of the amino acids in the reference sequence is deleted or substituted, or one or more amino acids are inserted into the sequence of the reference amino acid sequence. As a result of the alterations, the amino acid sequence variant has an amino acid sequence which is at least 70% identical to the reference sequence, preferably at least 80% identical to the reference sequence, more preferably at least 90% identical, even more preferably at least 95% identical, and particularly preferably at least 99% identical to the reference sequence. Variant sequences which are at least 90% identical have no more than 10 alterations, i.e. any combination of deletions, insertions or substitutions, per 100 amino acids of the reference sequence.

In the context of (poly-)peptides/proteins, a "linear sequence" or a "sequence" is the order of amino acids in a peptide/protein in an amino to carboxyl terminal direction in which residues that neighbor each other in the sequence are contiguous in the primary structure of the peptide/protein.

While it is possible to have non-conservative amino acid substitutions in a "sequence variant", it is preferred in a "sequence variant" that the substitutions are conservative amino acid substitutions, in which the substituted amino acid has similar structural or chemical properties with the corresponding amino acid in the reference sequence. By way of example, conservative amino acid substitutions involve substitution of one aliphatic or hydrophobic amino acid, e.g. alanine, valine, leucine and isoleucine, with another; substitution of one hydroxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include the fusion to the N- or C-terminus of an amino acid sequence to a reporter molecule or an enzyme.

Typically, the sequence variants are functional sequence variants, i.e. the alterations in the sequence variants do not abolish the functionality of the respective reference sequence, in the present case for example the functionality of binding to HMGB1 and/or inhibiting HMGB1/CXCL12 interaction. Guidance in determining which nucleotides and amino acid residues, respectively, may be substituted, inserted or deleted without abolishing such functionality are found by using computer programs well known in the art.

As used herein, a nucleic acid sequence or an amino acid sequence "derived from" a designated nucleic acid, peptide, polypeptide or protein refers to the origin of the polypeptide. Preferably, the nucleic acid sequence or amino acid sequence which is derived from a particular sequence has an amino acid sequence that is essentially identical to that sequence or a portion thereof, from which it is derived, whereby the expression "essentially identical" includes sequence variants as defined above. Preferably, the nucleic acid sequence or amino acid sequence which is derived from a particular peptide or protein, is derived from the corresponding domain in the particular peptide or protein. Thereby, "corresponding" refers in particular to the same functionality. For example, an "extracellular domain" corresponds to another "extracellular domain" (of another protein), or a "transmembrane domain" corresponds to another "transmembrane domain" (of another protein). "Corresponding" parts of peptides, proteins and nucleic acids are thus easily identifiable to one of ordinary skill in the art, e.g. by the use of computer programs, which are able to predict protein domains, such as transmembrane domains, signal domains, binding domains, or the like. Likewise, sequences "derived from" other sequence are usually easily identifiable to one of ordinary skill in the art as having its origin in the sequence.

Preferably, a nucleic acid sequence or an amino acid sequence derived from another nucleic acid, peptide, polypeptide or protein may be identical to the starting nucleic acid, peptide, polypeptide or protein (from which it is derived). However, a nucleic acid sequence or an amino acid sequence derived from another nucleic acid, peptide, polypeptide or protein may also have one or more mutations relative to the starting nucleic acid, peptide, polypeptide or protein (from which it is derived), in particular a nucleic acid sequence or an amino acid sequence derived from another nucleic acid, peptide, polypeptide or protein may be a functional sequence variant as described above of the starting nucleic acid, peptide, polypeptide or protein (from which it is derived). For example, in a peptide/protein one or more amino acid residues may be substituted with other amino acid residues or one or more amino acid residue insertions or deletions may occur.

As used herein, the term "mutation" relates to a change in the nucleic acid sequence and/or in the amino acid sequence in comparison to a reference sequence, e.g. a corresponding genomic sequence. A mutation, e.g. in comparison to a genomic sequence, may be, for example, a (naturally occurring) somatic mutation, a spontaneous mutation, an induced mutation, e.g. induced by enzymes, chemicals or radiation, or a mutation obtained by site-directed mutagenesis (molecular biology methods for making specific and intentional changes in the nucleic acid sequence and/or in the amino acid sequence). Thus, the terms "mutation" or "mutating" shall be understood to also include physically making a mutation, e.g. in a nucleic acid sequence or in an amino acid sequence. A mutation includes substitution, deletion and insertion of one or more nucleotides or amino acids as well as inversion of several successive nucleotides or amino acids. To achieve a mutation in an amino acid sequence, preferably a mutation may be introduced into the nucleotide sequence encoding said amino acid sequence in order to express a (recombinant) mutated polypeptide. A mutation may be achieved e.g., by altering, e.g., by site-directed mutagenesis, a codon of a nucleic acid molecule encoding one amino acid to result in a codon encoding a different amino acid, or by synthesizing a sequence variant, e.g., by knowing the nucleotide sequence of a nucleic acid molecule encoding a polypeptide and by designing the synthesis of a nucleic acid molecule comprising a nucleotide sequence encoding a variant of the polypeptide without the need for mutating one or more nucleotides of a nucleic acid molecule.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration and/or quality of life.

As used herein, reference to "treatment" of a subject or patient is intended to include prevention, prophylaxis, attenuation, amelioration and therapy. The terms "subject" or "patient" are used interchangeably herein to mean all mammals including humans. Examples of subjects include humans, cows, dogs, cats, horses, goats, sheep, pigs, and rabbits. Preferably, the subject or patient is a human.

Doses are often expressed in relation to the bodyweight. Thus, a dose which is expressed as [g, mg, or other unit]/kg (or g, mg etc.) usually refers to [g, mg, or other unit] "per kg (or g, mg etc.) bodyweight", even if the term "bodyweight" is not explicitly mentioned.

The terms "binding" and, in particular, "specifically binding" and similar reference do not encompass non-specific sticking.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Peptide Inhibitors of the HMGB1/CXCL12 Interaction

In a first aspect the present invention provides a peptide consisting of an amino acid sequence according to any one of SEQ ID NOs 1-58; or of an amino acid sequence having at least 75% sequence identity to any one of SEQ ID NOs 1-58. In other words, the present invention provides a peptide consisting of an amino acid sequence according to any one of SEQ ID NOs 1-58; or a sequence variant thereof as described above.

In contrast to previously identified inhibitors of the HMGB1/CXCL12 interaction, the present invention provides peptide inhibitors. Peptides are known for being highly selective and efficacious and, at the same time, relatively safe and well tolerated. The present inventors identified various peptide inhibitors of the HMGB1/CXCL12 interaction.

Table 1 shows exemplary peptide inhibitors of the HMGB1/CXCL12 interaction:

| SEQ ID NO | Sequence | Peptide name |
|---|---|---|
| SEQ ID NO: 1 | GYHYERWIH | HBP08 |
| SEQ ID NO: 2 | HWTLANWCR | HBP07 |
| SEQ ID NO: 3 | WISNWILMW | HBP05 |
| SEQ ID NO: 4 | YHICWYGDY | HBP12 |
| SEQ ID NO: 5 | HEMYWEDEW | HBP01 |
| SEQ ID NO: 6 | IDLRFFMRQ | HBP02 |
| SEQ ID NO: 7 | FAFELIQTD | HBP03 |
| SEQ ID NO: 8 | CIPMMMHAW | HBP04 |
| SEQ ID NO: 9 | TWNIHFADH | HBP06 |
| SEQ ID NO: 10 | QFMKNCEEM | HBP09 |
| SEQ ID NO: 11 | SINWHMYVN | HBP10 |
| SEQ ID NO: 12 | MYRENQPTR | HBP11 |
| SEQ ID NO: 13 | WLWYEWGWQ | HBP13 |
| SEQ ID NO: 14 | DYCWKIMTQ | |
| SEQ ID NO: 15 | WCHFFFPHW | |
| SEQ ID NO: 16 | MKSSDCCLE | |
| SEQ ID NO: 17 | EWFVMKHLN | |
| SEQ ID NO: 18 | MIRDQILHN | |
| SEQ ID NO: 19 | WHQLTEHWI | |
| SEQ ID NO: 20 | HDHDFWAWY | |
| SEQ ID NO: 21 | WQWHQFQGR | |
| SEQ ID NO: 22 | VMASWQHGL | |
| SEQ ID NO: 23 | LDNFLGDHW | |
| SEQ ID NO: 24 | PRMGWEKPE | |
| SEQ ID NO: 25 | WICVWHHAS | |
| SEQ ID NO: 26 | IRWCVDARY | |
| SEQ ID NO: 27 | WNAMSFCCS | |
| SEQ ID NO: 28 | IFHIMTEMW | |
| SEQ ID NO: 29 | FDRPRYRTT | |
| SEQ ID NO: 30 | QIEDMPTSK | |
| SEQ ID NO: 31 | FDCMMDMTK | |
| SEQ ID NO: 32 | NTVALKLRD | |
| SEQ ID NO: 33 | YHYHMLMQS | |
| SEQ ID NO: 34 | NITHNVWHR | |
| SEQ ID NO: 35 | DRNLEVEQI | |
| SEQ ID NO: 36 | HYNKWKHQE | |
| SEQ ID NO: 37 | ICMPPNTKN | |
| SEQ ID NO: 38 | SMIPVQEAS | |
| SEQ ID NO: 39 | YQRNELEYL | |
| SEQ ID NO: 40 | HYFDMLHFH | |
| SEQ ID NO: 41 | SHYFKHSNF | |
| SEQ ID NO: 42 | FIKQMEEST | |
| SEQ ID NO: 43 | KYQWMHYTP | |
| SEQ ID NO: 44 | HIWREYHYG | all D amino acids; HBP08-RI |
| SEQ ID NO: 45 | AYHYERWIH | HBP08-A1 |
| SEQ ID NO: 46 | GAHYERWIH | HBP08-A2 |
| SEQ ID NO: 47 | GYAYERWIH | HBP08-A3 |
| SEQ ID NO: 48 | GYHAERWIH | HBP08-A4 |

-continued

| SEQ ID NO | Sequence | Peptide name |
|---|---|---|
| SEQ ID NO: 49 | GYHYARWIH | HBP08-A5 |
| SEQ ID NO: 50 | GYHYEAWIH | HBP08-A6 |
| SEQ ID NO: 51 | GYHYERAIH | HBP08-A7 |
| SEQ ID NO: 52 | GYHYERWAH | HBP08-A8 |
| SEQ ID NO: 53 | GYHYERWIA | HBP08-A9 |
| SEQ ID NO: 54 | GDHYERWIH | HBP08-D2 |
| SEQ ID NO: 55 | GYHYERWIK | HBP08-K9 |
| SEQ ID NO: 56 | GKHYERWIH | HBP08-K2 |
| SEQ ID NO: 57 | HYWYERWEH | XHBP08 |
| SEQ ID NO: 58 | ERWIH | Pentapept-2 |

The peptides according to the present invention are those shown in Table 1 and sequence variants thereof having at least 75% sequence identity. In other words, the nonapeptides according to SEQ ID NO: 1-57 may comprise (exactly) one or two mutations (as compared to SEQ ID NO: 1-57). Accordingly, the peptides have at least 75%, preferably at least 88% sequence identity, with any one of the sequences according to SEQ ID NO: 1-58. In general, preferred mutations are conservative amino acid mutations as described above.

The peptide may consist of an amino acid sequence according to any one of SEQ ID NOs 1-13, 44 and 57; or of an amino acid sequence having at least 75% sequence identity to any one of SEQ ID NOs 1-13, 44 and 57. For example, the peptide may consist of an amino acid sequence having at least 88% sequence identity to any one of SEQ ID NOs 1-13, 44 and 57 (i.e., exactly one mutation as compared to SEQ ID NOs 1-13, 44 and 57).

For example, the peptide may consist of an amino acid sequence according to any one of SEQ ID NOs 1-4; or of an amino acid sequence having at least 75% sequence identity to any one of SEQ ID NOs 1-4. In particular, the peptide may consist of an amino acid sequence according to SEQ ID NO: 1 or 2; or of an amino acid sequence having at least 75% sequence identity to SEQ ID NO: 1 or 2.

Preferably, the peptide has an amino acid sequence of SEQ ID NO: 1 ("HBP08") or the peptide is derived from HBP08 (SEQ ID NO: 1). Exemplary peptides derived from HBP08 (SEQ ID NO: 1) include the peptides as set forth in SEQ ID NOs 44-58. Accordingly, the peptide may consist of an amino acid sequence according to any one of SEQ ID NOs 1 and 44-58; or of an amino acid sequence having at least 75% sequence identity to any one of SEQ ID NOs 1 and 44-58. For example, the peptide may consist of an amino acid sequence having at least 88% sequence identity to any one of SEQ ID NOs 1 and 44-58 (i.e., exactly one mutation as compared to SEQ ID NOs 1 and 44-58).

More preferably, the peptide consists of an amino acid sequence according to any one of SEQ ID NOs 1, 44-49, 51, 52 and 54-57; or of an amino acid sequence having at least 75% sequence identity to any one of SEQ ID NOs 1, 44-49, 51, 52 and 54-57. For example, the peptide may consist of an amino acid sequence having at least 88% sequence identity to any one of SEQ ID NOs 1, 44-49, 51, 52 and 54-57 (i.e., exactly one mutation as compared to SEQ ID NOs 1, 44-49, 51, 52 and 54-57).

Even more preferably, the peptide consists of an amino acid sequence according to any one of SEQ ID NOs 1, 44-49, 51, 52, 54, 56 and 57; or of an amino acid sequence having at least 75% sequence identity to any one of SEQ ID NOs 1, 44-49, 51, 52, 54, 56 and 57. For example, the peptide may consist of an amino acid sequence having at least 88% sequence identity to any one of SEQ ID NOs 1, 44-49, 51, 52, 54, 56 and 57 (i.e., exactly one mutation as compared to SEQ ID NOs 1, 44-49, 51, 52, 54, 56 and 57). In the sequence variants it is preferred that the amino acids Trp7 and His9 are maintained (i.e., not mutated).

In a specific embodiment, the peptide consists of an amino acid sequence according to SEQ ID NO: 1 ("HBP08") or of an amino acid sequence having at least 75% or 88% sequence identity to SEQ ID NO: 1, preferably wherein in the sequence variant Trp7 and His9 of SEQ ID NO: 1 are maintained. In addition, also His3 of SEQ ID NO: 1 may be maintained in the sequence variant. Furthermore, also Arg6 of SEQ ID NO: 1 may be maintained in the sequence variant.

In another specific embodiment, the peptide consists of an all-D amino acid sequence according to SEQ ID NO: 44 ("HBP08-RI") or of an amino acid sequence having at least 75% or 88% sequence identity to the all-D amino acid sequence of SEQ ID NO: 44, preferably wherein in the sequence variant His1 and Trp3 of SEQ ID NO: 44 are maintained. In addition, also His7 of SEQ ID NO: 44 may be maintained in the sequence variant. Furthermore, also Arg4 of SEQ ID NO: 44 may be maintained in the sequence variant. The peptide having an all-D amino acid sequence according to SEQ ID NO: 44 ("HBP08-RI") is the D-retro-inverso version of the peptide of SEQ ID NO: 1 ("HBP08").

In another specific embodiment, the peptide consists of an amino acid sequence according to SEQ ID NO: 57 ("XHBP08") or of an amino acid sequence having at least 75% or 88% sequence identity to SEQ ID NO: 57, preferably wherein in the sequence variant Trp7 and His9 of SEQ ID NO: 57 are maintained. In addition, also Arg6 of SEQ ID NO: 1 may be maintained in the sequence variant.

The peptide according to the present invention may be modified at its N-terminus. Moreover, the peptide according to the present invention may be modified at its C-terminus. For example, the peptide having an amino acid sequence according to SEQ ID NO: 44 may be modified at its N-terminus and/or at its C-terminus. The C-Terminus may preferably be modified by an amide modification, whereas the N-terminus may be modified by any suitable NH$_2$-protection group, such as e.g. acetylation. In particular, the peptide according to the present invention may be modified at its C-terminus by an amide modification, such as an amidation; and/or at its N-terminus by an NH$_2$-protection group, such as acetylation.

In particular, the peptide according to the present invention binds to HMGB1, preferably to BoxA of HMGB1. Thereby, HMGB1 interaction with CXCL12 can be inhibited. Accordingly, the peptide according to the present invention in particular reduces or inhibits CXCL12/HMGB1 interaction. The Kd value for binding of the peptide to HMGB1 is less than 100 µM, preferably less than 50 µM, more preferably less than 20 µM.

In general, methods for testing binding to HMGB1 (in particular BoxA of HMGB1) and/or reduction/inhibition of CXCL12/HMGB1 interaction are known in the art. Preferred methods are those used in the examples of the present specification. For example, the binding affinity ($K_d$) between HMGB1 and a peptide may be measured by microscale thermophoresis (MST), e.g. as described in Jerabek-Willemsen M, Wienken C J, Braun D, Baaske P, & Duhr S (2011)

Molecular interaction studies using microscale thermophoresis. *Assay Drug Dev Technol* 9(4):342-353, or in Example 5 of the present specification. As used herein, "$K_d$" refers to the dissociation constant for a given interaction, such as a peptide-HMGB1 interaction. For example, for the interaction of the peptide according to the present invention and HMGB1, it is the concentration of the individual components of the interaction divided by the concentration of the complex.

Reduction/inhibition of CXCL12/HMGB1 interaction may be evaluated, for example, by assessing migration/chemotaxis of cells (e.g., (human) blood cells, such as monocytes) in response to a sub-optimal CXCL12 concentration in the presence of HMGB1. CXCL12 and HMGB1 may be pre-incubated with a potential inhibitor of interaction and cell migration with and without presence of the inhibitor may be compared. Examples 2 and 4 of the present specification provide exemplified methods for testing reduction/inhibition of CXCL12/HMGB1 interaction.

Protein Comprising the Peptide According to the Invention, Virus-Like Particle and Protein Nanoparticle In a further aspect the present invention provides a protein comprising the peptide according to the present invention. For example, the protein may consist of the peptide according to the present invention. However, it is preferred that the protein comprises (i) the peptide according to the present invention and (ii) an additional amino acid sequence, preferably providing a synergistic functionality and/or an additional functionality to the protein. In other words, such an additional amino acid sequence may preferably provide a functionality, in addition to the peptide's functionality (e.g., as inhibitor of CXCL12/HMGB1 interaction), which may be synergistic with to the peptide's functionality. A non-limiting example of such functionalities may be a targeting functionality.

To this end, the protein according to the present invention may be a fusion protein. Fusion proteins typically comprise two or more distinct functionalities. Accordingly, fusion proteins typically comprise "parts" from different sources, for example a fusion protein comprises distinct proteins/peptides encoded by at least two distinct genes or parts of (distinct) genes. Accordingly, fusion proteins may be also referred to as "chimeric proteins". Even though fusion proteins may, in general, occur in nature, e.g., when a complex mutation, such as a chromosomal translocation, tandem duplication, or retrotransposition creates a novel coding sequence containing parts of the coding sequences from two different genes (for example in cancer cells), recombinant fusion proteins (which do not occur in nature) are preferred. Recombinant fusion proteins do not occur in nature in that combination.

For example, the protein according to the present invention further comprises targeting moiety, such as a targeting peptide. In general, a targeting peptide is peptide chain that directs the transport of a protein to a specific location, for example to a specific cell type, into cells or to a specific region in the cell, including the nucleus, mitochondria, endoplasmic reticulum (ER), chloroplast, apoplast, peroxisome and plasma membrane. Targeting peptides may optionally be cleaved from the protein, e.g. by signal peptidases, after the proteins are transported to the specific location. Preferred targeting peptides include antibodies and fragments thereof, such as scFV. For example, such antibodies or antibody fragments may be directed to surface molecules of specific cell types. For example, the targeting peptide may have a length of no more than 1000 amino acids, preferably of no more than 500 amino acids, more preferably of no more than 200 amino acids, even more preferably of no more than 100 amino acids, still more preferably of no more than 80 amino acids, particularly preferably of no more than 70 amino acids and most preferably of no more than 50 amino acids. For example, the targeting peptide may have a length from 3 to 70 amino acids.

The protein according to the present invention may further comprise linker sequences, as known in the art, for example "GS-linkers".

The protein according to the present invention has preferably a length of at least 20 amino acids, preferably at least 50 amino acids, preferably at least 60 amino acids, more preferably at least 70 amino acids, more preferably at least 80 amino acids, more preferably at least 90 amino acids, even more preferably at least 100 amino acids, even more preferably at least 150 amino acids, even more preferably at least 200 amino acids, still more preferably at least 250 amino acids, still more preferably at least 300 amino acids, most preferably at least 350 or at least 400 amino acids. In a further aspect the present invention also provides a virus-like particle comprising the comprising the peptide according to the present invention as described herein or the protein according to the present invention as described herein.

As used herein, a "virus-like particle" (also "VLP") refers in particular to a non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. Further, VLPs can be isolated by known techniques, e.g., density gradient centrifugation and identified by characteristic density banding. See, for example, Baker et al. (1991) Biophys. J. 60: 1445-1456; and Hagensee et al. (1994) J. Viral. 68:4503-4505; Vincente, J Invertebr Pathol., 2011; Schneider-Ohrum and Ross, Curr. Top. Microbial. Immunol., 354: 53073, 2012).

A virus-like particle comprising the peptide according to the present invention or the protein according to the present invention as described herein is thus in particular a virus-like particle (VLP) that includes the peptide or the protein according to the present invention, which comprises any one of SEQ ID NOs 1-58. Preferred embodiments of the VLP comprising the peptide according to the present invention or the protein according to the present invention correspond to preferred embodiments of the peptide according to the present invention or the protein according to the present invention.

In general, VLPs lack the viral components that are required for virus replication and thus represent a highly attenuated form of a virus. The VLP can display a polypeptide (e.g., the peptide according to the present invention or the protein according to the present invention). Virus like particles and methods of their production are known and familiar to the person of ordinary skill in the art, and viral proteins from several viruses are known to form VLPs, including human papillomavirus, HIV (Kang et al., Biol. Chem. 380: 353-64 (1999)), Semliki-Forest virus (Notka et al., Biol. Chem. 380: 341-52 (1999)), human polyomavirus (Goldmann et al., J. Virol. 73: 4465-9 (1999)), rota virus (Jiang et al., Vaccine 17: 1005-13 (1999)), parvovirus (Casal, Biotechnology and Applied Biochemistry, Vol 29, Part 2, pp 141-150 (1999)), canine parvovirus (Hurtado et al., J. Viral. 70: 5422-9 (1996)), hepatitis E virus (Li et al., J. Viral. 71: 35 7207-13 (1997)), and Newcastle disease virus. For example, a chimeric VLP containing the peptide according to the present invention can be a HBsAg-based VLP. The formation of such VLPs can be detected by any suitable technique. Examples of suitable techniques known in the art for detection of VLPs in a medium include, e.g., electron microscopy techniques, dynamic light scattering (DLS), selective chromatographic separation (e.g., ion exchange, hydrophobic interaction, and/or size exclusion chromatographic separation of the VLPs) and density gradient centrifugation.

In a further aspect the present invention also provides a protein nanoparticle comprising the peptide according to the present invention or the protein according to the present invention.

As used herein, a "protein nanoparticle" refers in particular to a multi-subunit, protein-based polyhedron shaped structure. The subunits are each composed of proteins or polypeptides (for example a glycosylated polypeptide), and, optionally of single or multiple features of the following: nucleic acids, prosthetic groups, organic and inorganic compounds. Non-limiting examples of protein nanoparticles include ferritin nanoparticles (see, e.g., Zhang, Y. Int. J. Mol. Sci., 12:5406-5421, 2011, incorporated by reference herein), encapsulin nanoparticles (see, e.g., Sutter et al., Nature Struct. and Mol. Biol., 15:939-947, 2008, incorporated by reference herein), Sulfur Oxygenase Reductase (SOR) nanoparticles (see, e.g., Urich et al., Science, 311:996-1000, 2006, incorporated by reference herein), lumazine synthase nanoparticles (see, e.g., Zhang et al., J. Mol. Biol., 306: 1099-1114, 2001) or pyruvate dehydrogenase nanoparticles (see, e.g., Izard et al., PNAS 96: 1240-1245, 1999, incorporated by reference herein). Ferritin, encapsulin, SOR, lumazine synthase, and pyruvate dehydrogenase are monomeric proteins that self-assemble into globular protein complexes that in some cases consists of 24, 60, 24, 60, and 60 protein subunits, respectively. Preferably, ferritin, encapsulin, SOR, lumazine synthase, or pyruvate dehydrogenase monomers are linked to the peptide according to the present invention or to the protein according to the present invention and self-assembled into a protein nanoparticle presenting the peptide according to the invention on its surface. Further preferred examples of protein nanoparticles, and methods for obtaining the same, are disclosed in Warangkana Lohcharoenkal, Liying Wang, Yi Charlie Chen, and Yon Rojanasakul, "Protein Nanoparticles as Drug Delivery Carriers for Cancer Therapy," BioMed Research International, vol. 2014, Article ID 180549, 12 pages, 2014. doi:10.1155/2014/180549, which is incorporated herein by reference.

A protein nanoparticle particle comprising the peptide according to the present invention as described herein is thus in particular a protein nanoparticle that includes the peptide according to the present invention or the protein according to the present invention. Preferred embodiments of the protein nanoparticle comprising the peptide according to the present invention or the protein according to the present invention correspond to preferred embodiments of the peptide according to the present invention or of the protein according to the present invention.

Preferably, the peptide according to the present invention or the protein according to the present invention is linked to the N- or C-terminus of a nanoparticle protein, such as a ferritin, encapsulin, SOR, lumazine synthase or pyruvate dehydrogenase protein, for example with a linker, such as a GS-linker known in the art. Constructs are preferably made in HEK 293 cells, in particular since fusion proteins may be secreted from those cells and self-assemble into nanoparticles. The nanoparticles can be purified using known techniques, for example by a few different chromatography procedures, e.g. Mono Q (anion exchange) followed by size exclusion (SUPEROSE® 6) chromatography.

Preferably, the protein nanoparticles has a molecular weight of from 100 to 5000 kDa, such as approximately 500 to 4600 kDa. More preferably, a Ferritin nanoparticle has an approximate molecular weight of about 650 kDa, an Encapsulin nanoparticle has an approximate molecular weight of about 2100 kDa, a SOR nanoparticle has an approximate molecular weight of about 1000 kDa, a lumazine synthase nanoparticle has an approximate molecular weight of about 4000 kDa, and a pyruvate dehydrogenase nanoparticle has an approximate molecular weight of about 4600 kDa, when the protein nanoparticle includes the peptide according to the present invention or the protein according to the present invention.

Nucleic Acid Molecules, Vectors and Cells

In another aspect, the invention also provides a nucleic acid molecule comprising a polynucleotide encoding the peptide according to the present invention as described above or the protein according to the present invention as described above.

As used herein, the terms "nucleic acid", "nucleic acid molecule" and "polynucleotide" are used interchangeably and are intended to include DNA molecules and RNA molecules. A nucleic acid molecule may be single-stranded or double-stranded, but preferably is double-stranded DNA. Examples of nucleic acid molecules and/or polynucleotides include, e.g., a recombinant polynucleotide, a vector, an oligonucleotide, an RNA molecule such as an rRNA, an mRNA, an miRNA, an siRNA, or a tRNA, or a DNA molecule such as a cDNA. The nucleic acid molecule may also be a vector as described below.

A nucleic acid molecule is a molecule comprising, preferably consisting of nucleic acid components. The term nucleic acid molecule preferably refers to DNA or RNA molecules. Preferably, a nucleic acid molecule is a polymer comprising or consisting of nucleotide monomers which are covalently linked to each other by phosphodiester-bonds of a sugar/phosphate-backbone. The term "nucleic acid molecule" also encompasses modified nucleic acid molecules, such as base-modified, sugar-modified or backbone-modified etc. DNA or RNA molecules.

It is also preferred that nucleic acid sequences according to the invention include nucleic acid sequences having at least 70%, at least 75%, at least 80%, at least 85%, at least 88%, at least 90%, at least 92%, at least 95%, at least 96%, at least 97%, at least 98% or at least 99% identity to the nucleic acid encoding a peptide according to the present invention, for example to the sequences according to any of SEQ ID NOs: 1-58. More preferably, the nucleic acid molecule according to the present invention comprises a the polynucleotide encoding any of the amino acid sequences according to any of SEQ ID NOs: 1-58.

In general, the nucleic acid molecule may be manipulated to insert, delete or alter certain nucleic acid sequences. Changes from such manipulation include, but are not limited to, changes to introduce restriction sites, to amend codon usage, to add or optimize transcription and/or translation regulatory sequences, etc. It is also possible to change the nucleic acid to alter the encoded amino acids. For example, it may be useful to introduce one or more (e.g., 1, 2, 3, 4, 5, 6, 7, 8, 9, 10, etc.) amino acid substitutions, deletions and/or insertions into the amino acid sequence. Such point mutations can modify effector functions, binding affinity, post-translational modifications, etc., can introduce amino acids for the attachment of covalent groups (e.g., labels) or can introduce tags (e.g., for purification purposes). Mutations can be introduced in specific sites or can be introduced at random, followed by selection (e.g., molecular evolution). For instance, one or more nucleic acids encoding the peptide according to the present invention can be randomly or directionally mutated to introduce different properties in the encoded amino acids. Such changes can be the result of an iterative process wherein initial changes are retained and new changes at other nucleotide positions are introduced. Further, changes achieved in independent steps may be combined. Different properties introduced into the encoded amino acids may include, but are not limited to, enhanced affinity.

In another aspect the present invention also provides a vector, for example an expression vector, comprising a nucleic acid molecule according to the present invention. Preferably, a vector comprises a nucleic acid molecule as described above.

The term "vector" refers to a nucleic acid molecule, preferably to a recombinant nucleic acid molecule, i.e. a nucleic acid molecule which does not occur in nature. A vector in the context of the present invention is suitable for incorporating or harboring a desired nucleic acid sequence. Such vectors may be storage vectors, expression vectors, cloning vectors, transfer vectors etc. A storage vector is a vector which allows the convenient storage of a nucleic acid molecule. Thus, the vector may comprise a sequence corresponding, e.g., to a desired peptide or protein according to the present invention. An expression vector may be used for production of expression products such as RNA, e.g. mRNA, or peptides, polypeptides or proteins. For example, an expression vector may comprise sequences needed for transcription of a sequence stretch of the vector, such as a promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule. For example, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

In a further aspect, the present invention also provides cell (a) expressing the peptide or protein according to the present invention; and/or (b) comprising the vector according the present invention.

As used herein, the terms "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

Examples of such cells include but are not limited to, eukaryotic cells, e.g., yeast cells, animal cells or plant cells. Preferably, the cells are mammalian cells, more preferably a mammalian cell line. Preferred examples include human cells, CHO cells, HEK293T cells, PER.C6 cells, NSO cells, human liver cells, myeloma cells or hybridoma cells.

In particular, the cell may be transfected with a vector according to the present invention, preferably with an expression vector. The term "transfection" refers to the introduction of nucleic acid molecules, such as DNA or RNA (e.g. mRNA) molecules, into cells, preferably into eukaryotic cells. In the context of the present invention, the term "transfection" encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

Moreover, the cells of the present invention may be transfected stably or transiently with the vector according to the present invention, e.g. for expressing the peptide or protein according to the present invention. Preferably, the cells are stably transfected with the vector according to the present invention, for example encoding the peptide or protein according to the present invention. Alternatively, it is also preferred that the cells are transiently transfected with the vector according to the present invention, for example encoding the peptide or protein according to the present invention.

Compositions, Uses and Methods

In a further aspect the present invention provides a composition comprising one or more of:
(i) the peptide according to the present invention;
(ii) the protein according to the present invention;
(iii) the nucleic acid encoding the protein or the peptide according to the present invention;
(iv) the virus-like particle according to the present invention;
(v) the protein nanoparticle according to the present invention;
(vi) the vector comprising the nucleic acid according to the present invention; and/or
(vii) the cell expressing the peptide according to the present invention, or comprising the vector according to the present invention.

In other words, the present invention also provides a composition comprising the peptide according to the present invention, the protein according to the present invention, the virus-like particle according to the present invention, the protein nanoparticle according to the present invention, the nucleic acid according to the present invention, the vector according to the present invention and/or the cell according to the present invention.

Preferably, the composition comprises the peptide according to the present invention and/or the protein according to the present invention.

The composition may optionally also contain a carrier, diluent and/or excipient.

In particular, the composition is a pharmaceutical composition, which may optionally also comprise a pharmaceutically acceptable carrier, diluent and/or excipient. Although the carrier or excipient may facilitate administration, it should preferably not itself induce the production of antibodies harmful to the individual receiving the composition. Nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles. In general, pharmaceutically acceptable carriers in a pharmaceutical composition according to the present invention may be active components or inactive components. Preferably, the pharmaceutically acceptable carrier in a pharmaceutical composition according to the present invention is not an active component in respect to CXCL12/HMGB1 interaction.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in a pharmaceutical composition may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the subject.

Pharmaceutical compositions of the invention may be prepared in various forms. For example, the compositions may be prepared as injectables, either as liquid solutions or suspensions. Solid forms suitable for solution in, or suspension in, liquid vehicles prior to injection can also be prepared (e.g., a lyophilized composition, similar to Synagis™ and Herceptin™, for reconstitution with sterile water containing a preservative). The composition may be prepared for topical administration e.g., as an ointment, cream or powder. The composition may be prepared for oral administration e.g., as a tablet or capsule, as a spray, or as a syrup (optionally flavored). The composition may be prepared for pulmonary administration e.g., as an inhaler, using a fine powder or a spray. The composition may be prepared as a suppository or pessary. The composition may be prepared for nasal, aural or ocular administration e.g., as drops. The composition may be in kit form, designed such that a combined composition is reconstituted just prior to administration to a subject. For example, a lyophilized peptide/protein may be provided in kit form with sterile water or a sterile buffer.

It is preferred that the active ingredient in the composition is the peptide according to the present invention, the protein according to the present invention, the protein nanoparticle according to the present invention and/or the virus-like particle according to the present invention. As such, it (the peptide, the protein, etc.) may be susceptible to degradation in the gastrointestinal tract. Thus, if the composition is to be administered by a route using the gastrointestinal tract, the composition may contain agents which protect the peptide, the protein, the protein nanoparticle or the virus-like particle from degradation but which release it once it has been absorbed from the gastrointestinal tract.

A thorough discussion of pharmaceutically acceptable carriers is available in Gennaro (2000) Remington: The Science and Practice of Pharmacy, 20th edition, ISBN: 0683306472.

Pharmaceutical compositions of the invention generally have a pH between 5.5 and 8.5, in some embodiments this may be between 6 and 8, and in other embodiments about 7. The pH may be maintained by the use of a buffer. The composition may be sterile and/or pyrogen free. The composition may be isotonic with respect to humans. In one embodiment pharmaceutical compositions of the invention are supplied in hermetically-sealed containers.

Within the scope of the invention are compositions present in several forms of administration; the forms include, but are not limited to, those forms suitable for parenteral administration, e.g., by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the peptide/protein may be in dry form, for reconstitution before use with an appropriate sterile liquid. A vehicle is typically understood to be a material that is suitable for storing, transporting, and/or administering a compound, such as a pharmaceutically active compound, in particular the peptide/protein according to the present invention. For example, the vehicle may be a physiologically acceptable liquid, which is suitable for storing, transporting, and/or administering a pharmaceutically active compound, in particular the peptide/protein according to the present invention. Once formulated, the compositions of the invention can be administered directly to the subject. In one embodiment the compositions are adapted for administration to mammalian, e.g., human subjects.

The pharmaceutical compositions of this invention may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions of the invention. Preferably, the pharmaceutical composition may be prepared for oral administration, e.g. as tablets, capsules and the like, for topical administration, or as injectable, e.g. as liquid solutions or suspensions, whereby it is particularly preferred that the pharmaceutical composition is an injectable. Solid forms suitable for solution in, or suspension in, liquid vehicles prior to injection are also be preferred, e.g. that the pharmaceutical composition is in lyophilized form.

For injection, e.g. intravenous, cutaneous or subcutaneous injection, or injection at the site of affliction, the active ingredient will preferably be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Whether it is a polypeptide, peptide, or nucleic acid molecule, other pharmaceutically useful compound according to the present invention that is to be given to an individual, administration is preferably in a "prophylactically effective amount" or a "therapeutically effective amount" (as the case may be), this being sufficient to show benefit to the individual. The actual amount administered, and rate and time-course of administration, will depend on the nature and severity of what is being treated. For injection, the pharmaceutical composition according to the present invention may be provided for example in a pre-filled syringe.

The inventive pharmaceutical composition as defined above may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient, i.e. the inventive transporter cargo conjugate molecule as defined above, is combined with emulsifying and suspending agents. If desired, certain sweetening, flavoring or coloring agents may also be added.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the inventive pharmaceutical composition, particularly its components as defined above, suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the inventive pharmaceutical composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

Dosage treatment may be a single dose schedule or a multiple dose schedule. In particular, the pharmaceutical composition may be provided as single-dose product. Preferably, the amount of the peptide/protein in the pharmaceutical composition—in particular if provided as single-dose product—does not exceed 200 mg, more preferably does not exceed 100 mg, and even more preferably does not exceed 50 mg.

The pharmaceutical composition according to the present invention may be administered once or repeatedly. For example, the pharmaceutical composition according to the present invention may be administered daily, e.g. once or several times per day, e.g. once, twice, three times or four times per day, preferably once or twice per day, more preferable once per day, for 1, 2, 3, 4, 5, 6, 7, 8, 9, 10, 11, 12, 13, 14, 15, 16, 17, 18, 19, 20 or 21 or more days, e.g. daily for 1, 2, 3, 4, 5, 6 months. Preferably, the pharmaceutical composition according to the present invention may be administered weekly, e.g. once or twice per week, for 1, 2, 3, 4, 5, 6, 7, 8, 9, 10, 11, 12, 13, 14, 15, 16, 17, 18, 19, 20 or 21 or more weeks, e.g. weekly for 1, 2, 3, 4, 5, 6, 7, 8, 9, 10, 11, or 12 months or weekly for 2, 3, 4, or 5 years. Moreover, the pharmaceutical composition according to the present invention may be preferably administered monthly, e.g. once per month or, more preferably, every second month for 1, 2, 3, 4, or 5 or more years. It is also preferred that the administration continues for the lifetime. In addition, one single administration only is also envisaged.

In particular, it is preferred that for a single dose, e.g. a daily, weekly or monthly dose, preferably for a weekly dose, the amount of the peptide/protein in the pharmaceutical composition according to the present invention, does not exceed 1 g, preferably does not exceed 500 mg, more preferably does not exceed 200 mg, even more preferably does not exceed 100 mg, and particularly preferably does not exceed 50 mg.

Pharmaceutical compositions typically include an "effective" amount of the peptide/protein of the invention, i.e. an amount that is sufficient to treat, ameliorate, attenuate or prevent a desired disease or condition, or to exhibit a detectable therapeutic effect. Therapeutic effects also include reduction or attenuation in pathogenic potency or physical symptoms. The precise effective amount for any particular subject will depend upon their size, weight, and health, the nature and extent of the condition, and the therapeutics or combination of therapeutics selected for administration. The effective amount for a given situation is determined by routine experimentation and is within the judgment of a clinician. For purposes of the present invention, an effective dose will generally be from about 0.005 to about 100 mg/kg, preferably from about 0.0075 to about 50 mg/kg, more preferably from about 0.01 to about 10 mg/kg, and even more preferably from about 0.02 to about 5 mg/kg, of the peptide of the present invention (e.g. amount of the peptide in the pharmaceutical composition) in relation to the bodyweight (e.g., in kg) of the individual to which it is administered.

In one embodiment, a composition of the invention may include the peptide/protein of the invention, wherein the peptide/protein may make up at least 50% by weight (e.g., 60%, 70%, 75%, 80%, 85%, 90%, 95%, 96%, 97%, 98%, 99% or more) of the total protein in the composition. In such a composition, the peptides/proteins are preferably in purified form.

The present invention also provides a method of preparing a pharmaceutical composition comprising the steps of: (i) preparing a peptide/protein of the invention; and (ii) admixing the purified peptide/protein with one or more pharmaceutically-acceptable carriers.

As an alternative to delivering peptides/proteins for therapeutic purposes, it is possible to deliver nucleic acid (typically DNA) that encodes the peptide/protein to a subject, such that the nucleic acid can be expressed in the subject in situ to provide a desired therapeutic effect. Suitable gene therapy and nucleic acid delivery vectors are known in the art.

Pharmaceutical compositions may include an antimicrobial particularly if packaged in a multiple dose format. They may comprise detergent e.g., a Tween (polysorbate), such as Tween 80. Detergents are generally present at low levels e.g., less than 0.01%. Compositions may also include sodium salts (e.g., sodium chloride) to give tonicity. For example, a concentration of 10±2 mg/ml NaCl is typical.

Further, pharmaceutical compositions may comprise a sugar alcohol (e.g., mannitol) or a disaccharide (e.g., sucrose or trehalose) e.g., at around 15-30 mg/ml (e.g., 25 mg/ml), particularly if they are to be lyophilized or if they include material which has been reconstituted from lyophilized material. The pH of a composition for lyophilization may be adjusted to between 5 and 8, or between 5.5 and 7, or around 6.1 prior to lyophilization.

In a further aspect, the present invention provides the use of (i) the peptide according to the present invention;
(ii) the protein according to the present invention;
(iii) the nucleic acid encoding the protein or the peptide according to the present invention;
(iv) the virus-like particle according to the present invention;
(v) the protein nanoparticle according to the present invention;
(vi) the vector comprising the nucleic acid according to the present invention;

(vii) the cell expressing the peptide according to the present invention, or comprising the vector according to the present invention; and/or (x) the (pharmaceutical) composition according to the present invention as a medicament.

In other words, the peptide according to the present invention, the protein according to the present invention, the nucleic acid according to the present invention, the virus-like particle according to the present invention, the protein nanoparticle according to the present invention, the vector according to the present invention, the cell according to the present invention, and/or the (pharmaceutical) composition according to the present invention may be provided for use in medicine.

In particular, the peptide according to the present invention, the protein according to the present invention, the nucleic acid according to the present invention, the virus-like particle according to the present invention, the protein nanoparticle according to the present invention, the vector according to the present invention, the cell according to the present invention, and/or the (pharmaceutical) composition according to the present invention may be used for prevention, amelioration and/or treatment of inflammation and/or an immune-related disease.

For example, the peptide according to the present invention, the protein according to the present invention, the nucleic acid according to the present invention, the virus-like particle according to the present invention, the protein nanoparticle according to the present invention, the vector according to the present invention, the cell according to the present invention, and/or the (pharmaceutical) composition according to the present invention may be used for prevention, amelioration and/or treatment of rheumatoid arthritis.

Accordingly, the present invention also provides a method of preventing and/or treating inflammation and/or an immune-related disease in a subject, wherein the method comprises administering to a subject in need thereof the peptide according to the present invention, the protein according to the present invention, the nucleic acid according to the present invention, the virus-like particle according to the present invention, the protein nanoparticle according to the present invention, the vector according to the present invention, the cell according to the present invention, and/or the (pharmaceutical) composition according to the present invention.

In general, the peptide according to the present invention, the protein according to the present invention, the virus-like particle according to the present invention, the protein nanoparticle according to the present invention, the nucleic acid according to the present invention, the vector according to the present invention, the cell according to the present invention or the pharmaceutical composition according to the present invention may be administered once or repeatedly.

Examples

In the following, particular examples illustrating various embodiments and aspects of the invention are presented. However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Figure 2:
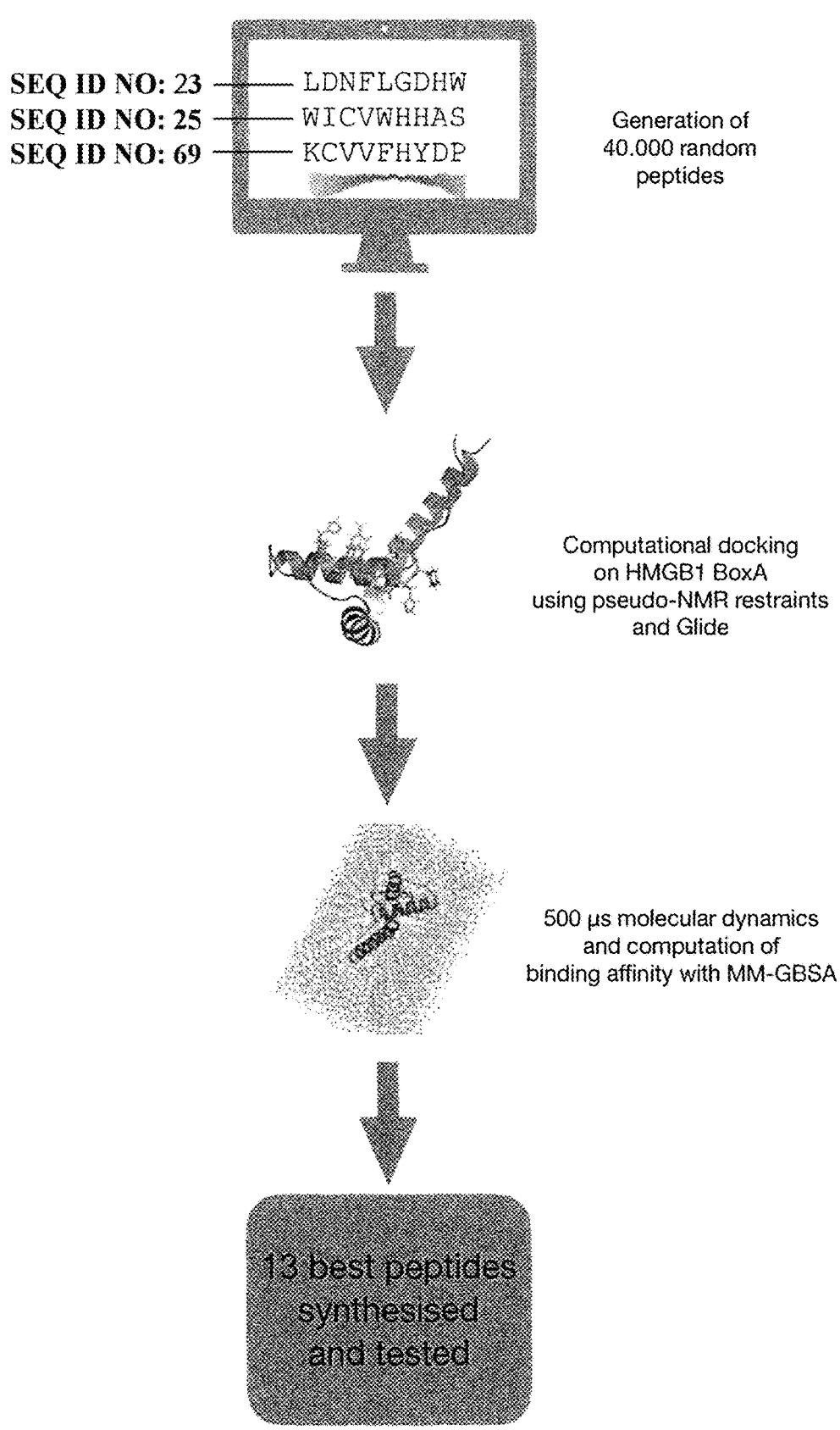
FIG. 2 shows for Example 1 a workflow diagram of the computational pipeline used for the identification of the binding peptide HBP08. Peptides with a randomly generated sequence are first docked using pseudo-NMR restraints and then re-docked with Glide. Finally, peptides are racked according to their binding free energy ΔG computed using MMGBSA with explicit water simulations of 500 ns.

Example 1: Identification of Peptide Inhibitors Targeting the CXCL12/HMGB1 Interaction To find novel and selective inhibitors of the CXCL12/HMGB1 interaction, a computational pipeline was developed which, by applying a series of computational filters, enabled the identification of high affinity peptide inhibitors of the CXCL12/HMGB1 interaction. FIG. 2 shows an overview over the method for identification of peptide inhibitors of the CXCL12/HMGB1 interaction.

A. Generation of a Model of the Glycyrrhizin and HMGB1 BoxA Interaction

Prior to this study, glycyrrhizin was the most potent and best characterized inhibitor of the CXCL12/HMGB1 heterocomplex (Schiraldi M, et al. (2012) HMGB1 promotes recruitment of inflammatory cells to damaged tissues by forming a complex with CXCL12 and signaling via CXCR4. *J Exp Med* 209(3):551-563). Due to the lack of a crystallographic or NMR structure of the complex, in order to obtain a template of the binding mode, a model of the glycyrrhizin and HMGB1 BoxA interaction was generated based on the results of previously reported NMR chemical shift studies obtained from previously published NMR analysis (Mollica L, et al. (2007) Glycyrrhizin binds to high-mobility group box 1 protein and inhibits its cytokine activities. *Chem Biol* 14(4):431-441). Namely, the model of the HMGB1-glycyrrhizin complex was built by ligand docking, starting from NMR HMGB1 structure solved by Yokoyama and co-workers available in the protein data bank (RCSB PDB) with the code 2YRQ. All the docking calculation were carried out using Glide (Schrödinger Inc.; www.schrodinger.com/glide) in the version 2016-4 (Friesner R A, et al. (2004) Glide: a new approach for rapid, accurate docking and scoring. 1. Method and assessment of docking accuracy. *J. Med. Chem.* 47(7):1739-1749). The grid necessary to perform docking was centered in the COG (center of geometry) of the protein and both, the enclosing and the bounding box, were set bigger than entire protein to allow a blind-docking, i.e. docking without previous knowledge of a binding site. Standard precision (SP) mode was used to score the resulting ligand-protein complexes.

Figure 3:
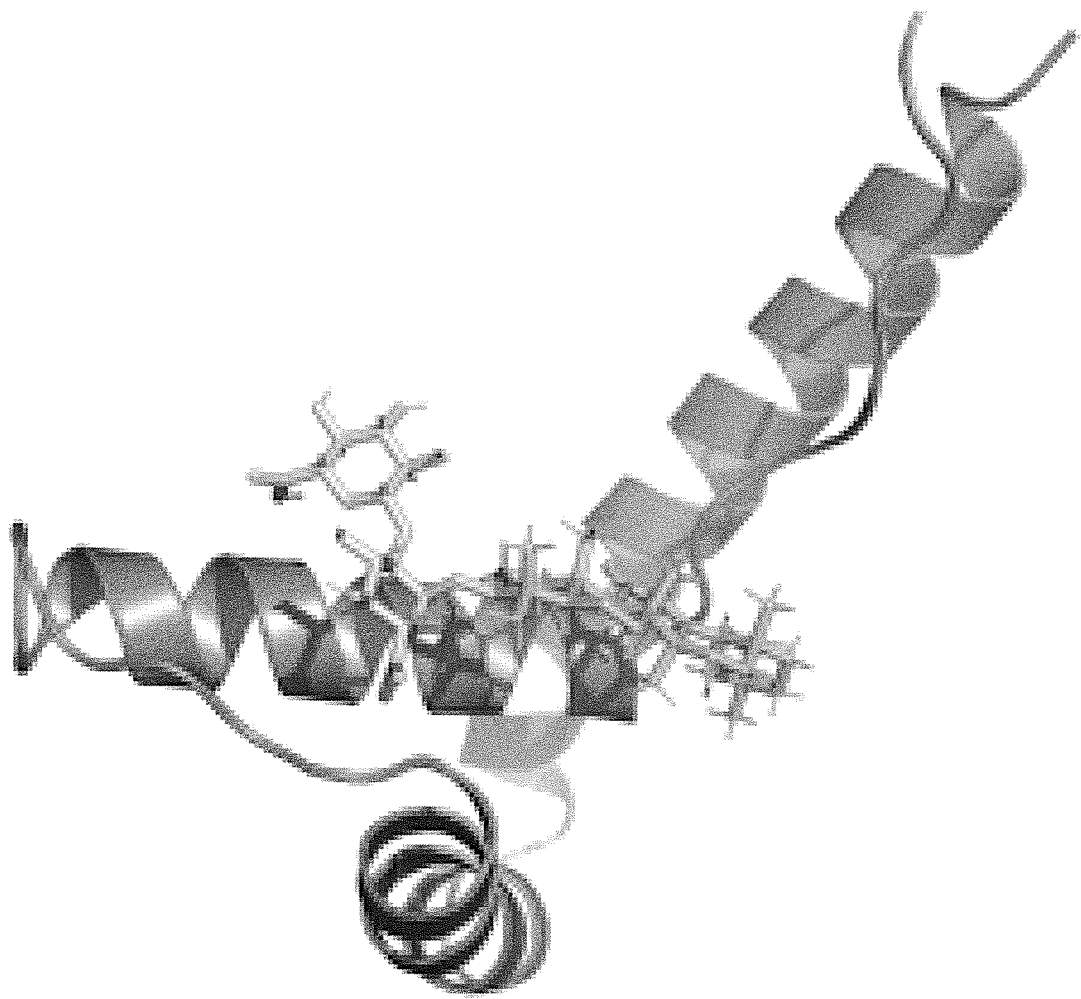
FIG. 3 shows for Example 1 the model of the glycyrrhizin-BoxA complex used to define the peptide binding site.
Figure 4A:
FIG. 4A-4M shows for Example 1 representations of the docking structures between BoxA of HMGB1 and the 13 selected peptides: HBP01 (FIG. 4A), HBP02 (FIG. 4B), HBP03 (FIG. 4C), HBP04 (FIG. 4D), HBP05 (FIG. 4E), HBP06 (FIG. 4F), HBP07 (FIG. 4G), HBP08 (FIG. 4H), HBP09 (FIG. 4I), HBP10 (FIG. 4J), HBP11 (FIG. 4K), HBP12 (FIG. 4L), and HBP13 (FIG. 4M).
Figure 4B:
Figure 4C:
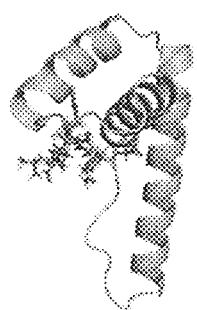
Figure 4D:
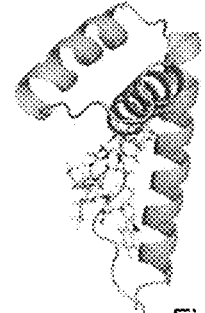
Figure 4E:
Figure 4F:
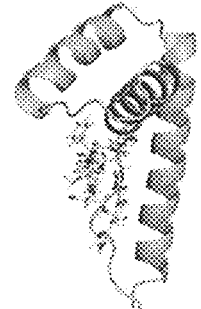
Figure 4G:
Figure 4H:
Figure 4I:
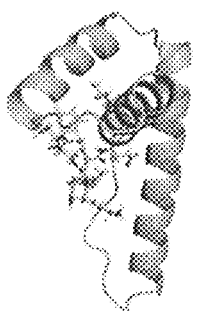
Figure 4J:
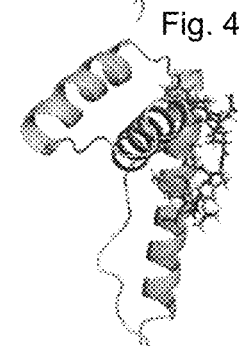
Figure 4K:
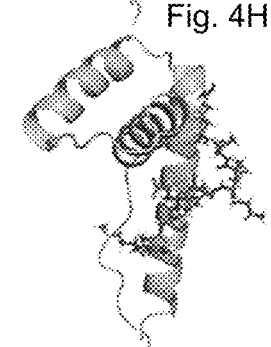
Figure 4L:
Figure 4M:

The twenty poses with the best Glide score were kept for further investigation. Finally, the structure with the best agreement with NMR chemical shifts perturbation (CSP) data by Mollica et al. (Mollica L, et al. (2007) Glycyrrhizin binds to high-mobility group box 1 protein and inhibits its cytokine activities. *Chem Biol* 14(4):431-441) was selected as the most likely representative model of the HMGB1-glycyrrhizin complex. The obtained model is shown in FIG. 3.

B Computational Design of Binding Peptides

To maximize the heterogeneity of the initial peptides, 40,000 peptides with randomly selected sequence were designed following a multistep process. First, the model of the BoxA-glycyrrhizin complex was used to define the target binding site for the peptides. To this end, all amino acids from BoxA, for which at least one carbon atom was at a distance smaller than 7.5 Å from a glycyrrhizin carbon atom, were selected. These gave a list of 17 amino acids, namely: LYS_12, MET_13, SER_14, SER_15, TRY_16, ALA_17, VAL_20, GLU_21, ARG_24, GLU_25, LYS_28, SER_35, VAL_36, ASN_37, PHE_38, PHE_41, SER_42.

Since the size of glycyrrhizin is approximatively equal to the length of a linear peptide of 9 amino acids, 40,000 nonapeptides (i.e., peptides having a length of 9 amino acids) with a random sequence were generated.

All 40,000 generated peptides were then docked in the glycyrrhizin binding site, namely, on the BoxA domain, using the torsional angular molecular dynamics (TMD) module (Stein E G, Rice L M, & Brunger A T (1997) Torsion-angle molecular dynamics as a new efficient tool for NMR structure calculation. *J Magn Reson* 124(1):154-164; Guntert P, Mumenthaler C, & Wuthrich K (1997) Torsion angle dynamics for NMR structure calculation with the new program DYANA. *J Mol Biol* 273(1):283-298) of the software package ALMOST (Fu B, et al. (2014) ALMOST: an all atom molecular simulation toolkit for protein structure determination. *J Comput Chem* 35(14):1101-1105). The docking of the peptides was guided by a set of 17 synthetic NMR-like ambiguous upper-distance restraints (Dominguez C, Boelens R, & Bonvin A M (2003) HADDOCK: a protein-protein docking approach based on biochemical or biophysical information. *J Am Chem Soc* 125(7):1731-1737) between the Cα atoms, i, of the residues of the binding site of BoxA and the Cα atoms, j, of the peptide, $$E_{pept}^i = \begin{cases} (d_{amb}^i - d_0)^2, & \text{if } d_{amb}^i > d_0 \\ 0, & \text{if } d_{amb}^i \leq d_0 \end{cases},$$

where $d_{amb}^i = (\Sigma_{j \in C\alpha pept} d_{ij}^{-6})^{-1/6}$ and $d_0 = 7.5$ Å.

For each peptide, the structure with the smallest distance restraint violations among the 25 generated, was then selected and minimized with the CHARMM 19 SASA implicit solvation force field (Ferrara P, Apostolakis J, & Caflisch A (2002) Evaluation of a fast implicit solvent model for molecular dynamics simulations. *Proteins* 46(1):24-33).

All peptides where then ranked according to their binding energy, $$\Delta E = E_{complex} - (E_{BoxA} + E_{pept}).$$

The best 100 peptides among the 40,000 peptides generated, were selected for the further analysis.

C Peptide Re-Docking

The best 100 ranking peptides were blindly re-docked with the program Glide (Tubert-Brohman I, Sherman W, Repasky M, & Beuming T (2013) Improved docking of polypeptides with Glide. *J Chem Inf Model* 53(7):1689-1699), to reduce the number of potential false positives using a consensus score (Kukol A (2011) Consensus virtual screening approaches to predict protein ligands. *Eur. J. Med. Chem.* 46(9):4661-4664).

To this end, the ability of the 100 peptides with the best CHARMM binding energy (as identified above) to form complexes with the BoxA domain of HMGB1 was then additionally assessed with the peptide-docking protocol of Glide (Celie P H N, et al. (2005) Crystal structure of acetylcholine-binding protein from *Bulinus truncatus* reveals the conserved structural scaffold and sites of variation in nicotinic acetylcholine receptors. *J. Biol. Chem.* 280(28):26457-26466), implemented in the Schrodinger suite for molecular modeling (Version 2016-2). Aiming to leave the algorithm free to explore the entire surface of the protein, also in this case blind docking was performed, using a grid positioned in the center of geometry (COG) and large enough to contain entire BoxA.

For each peptide, the 15 best poses were saved for further analysis, resulting in a total of 1,500 peptide-BoxA complexes. The 200 complexes with the best Glide score (GSCORE, a scoring function aimed at estimating binding affinity), were visually inspected and, for each peptide, only the best pose conserving some of the glycyrrhizin interaction was kept. Peptides without a pose in the top 200 solutions were discarded. At the end of this process, 57 peptides were retained for subsequent analysis.

D Molecular Dynamics (MD) and Binding Free Energy Calculations

To further asses the stability of the 57 selected peptide-BoxA complexes and to better estimate their affinity, the binding free energy (AG) for all remaining 57 BoxA/peptide complexes was computed by Molecular Mechanics—Generalized Born Surface Area (MM-GBSA) (Rastelli G, Del Rio A, Degliesposti G, & Sgobba M (2010) Fast and accurate predictions of binding free energies using MM-PBSA and MM-GBSA. *J Comput Chem* 31(4):797-810, Grazioso G, et al. (2009) Design of novel alpha7-subtype-preferring nicotinic acetylcholine receptor agonists: application of docking and MM-PBSA computational approaches, synthetic and pharmacological studies. *Bioorg Med Chem Lett* 19(22):6353-6357).

Several studies have shown that approximated free energy methods like MM-GBSA, especially when coupled with MD simulations, can be a valuable help in selection of active molecules in virtual screening investigations (Lammi C, Zanoni C, Aiello G, Arnoldi A, & Grazioso G (2016) Lupin Peptides Modulate the Protein-Protein Interaction of PCSK9 with the Low Density Lipoprotein Receptor in HepG2 Cells. *Sci Rep* 6:29931, Geng L, et al. (2015) Structure-based Design of Peptides with High Affinity and Specificity to HER2 Positive Tumors. *Theranostics* 5(10):1154-1165).

Therefore, a 0.5 μs long molecular dynamics (MD) simulation was performed in explicit water using AMBER16 for each of the 57 peptides obtained from docking calculations. All peptide-BoxA complexes were solvated in a water box with a minimum distance from the protein surface of 10 Å. The total charge of the system was neutralized adding a proper number of Cl$^-$/Na$^+$ ions. All molecular dynamics simulations were carried out using the ff14SB (Maier J A, et al. (2015) ff14SB: Improving the Accuracy of Protein Side Chain and Backbone Parameters from ff99SB. *Journal of Chemical Theory and Computation* 11(8):3696-3713) force field for the protein, the TIP3P model (Jorgensen W L, Chandrasekhar J, Madura J D, Impey R W, & Klein L M (1983) Comparison of simple potential functions for simulating liquid water. *J. Chem. Phys.* 79:926-935) for water, and the parameters proposed by Joung et al. (Joung I S & Cheatham T E (2008) Determination of alkali and halide monovalent ion parameters for use in explicitly solvated biomolecular simulations. *J. Phys. Chem. B* 112(18593145): 9020-9041) for the counter-ions. The peptide-BoxA complexes were first relaxed with a two-step computational protocol consisting of an energy minimization for 10,000 steps or until the energy gradient of 0.2 kcal/mol/Å$^2$ was reached, restraining the backbone atomic coordinates with a harmonic restraint (k=20 kcal/mol/Å$^2$), followed by an unrestrained energy minimization for 100,000 steps (or until an energy gradient of 0.0001 kcal/mol/Å$^2$ was reached). The systems were then heated to their final temperature of 300K in 40 ps. All simulations were run at constant volume, restraining the backbone coordinates (k=20 kcal/mol/Å$^2$) during the first 20 ps. Subsequently, the velocities were reassigned and the systems equilibrated for 20 ps at constant pressure (1 Atm). Finally, all complexes were simulated for 500 ns.

All the simulations were analyzed and only those 43 peptides (SEQ ID NO: 1-43), in which the peptide-BoxA complex was stable, were retained for MM-GBSA analysis. Accordingly, peptides detaching from the BoxA binding pocket during the simulations (14 out of 57) were considered unstable and not further analyzed in MM-GBSA calculations (Table 2).

TABLE 2

Results of the affinity prediction, performed by MM-GBSA, for the 57 peptides selected after docking calculations. The unbound states indicate that the peptide did not conserve its original binding mode over the simulation time.

| No | Sequence | SEQ ID NO. | Simulation | $\Delta G_{GB}$ | Std. Error | Name |
|---|---|---|---|---|---|---|
| 01 | HEMYWEDEW | 5 | OK | -52.8 | 0.3 | HBP01 |
| 02 | IDLRFFMRQ | 6 | OK | -52.0 | 0.3 | HBP02 |
| 03 | FAFELIQTD | 7 | OK | -51.7 | 0.4 | HBP03 |
| 04 | CIPMMMHAW | 8 | OK | -50.0 | 0.3 | HBP04 |
| 05 | WISNWILMW | 3 | OK | -45.9 | 0.3 | HBP05 |
| 06 | TWNIHFADH | 9 | OK | -45.6 | 0.5 | HBP06 |
| 07 | HWTLANWCR | 2 | OK | -45.2 | 0.4 | HBP07 |
| 08 | GYHYERWIH | 1 | OK | -45.1 | 0.5 | HBP08 |
| 09 | QFMKNCEEM | 10 | OK | -44.8 | 0.4 | HBP09 |
| 10 | SINWHMYVN | 11 | OK | -44.8 | 0.3 | HBP10 |
| 11 | MYRENQPTR | 12 | OK | -42.9 | 0.4 | HBP11 |
| 12 | YHICWYGDY | 4 | OK | -42.5 | 0.4 | HBP12 |
| 13 | WLWYEWGWQ | 13 | OK | -41.9 | 0.3 | HBP13 |
| 14 | DYCWKIMTQ | 14 | OK | -41.9 | 0.3 | |
| 15 | WCHFFFPHW | 15 | OK | -41.6 | 0.4 | |
| 16 | MKSSDCCLE | 16 | OK | -39.7 | 0.5 | |
| 17 | EWFVMKHLN | 17 | OK | -39.0 | 0.4 | |
| 18 | MIRDQILHN | 18 | OK | -38.9 | 0.4 | |
| 19 | WHQLTEHWI | 19 | OK | -38.2 | 0.5 | |
| 20 | HDHDFWAWY | 20 | OK | -37.5 | 0.2 | |
| 21 | WQWHQFQGR | 21 | OK | -35.9 | 0.3 | |
| 22 | VMASWQHGL | 22 | OK | -34.9 | 0.5 | |
| 23 | LDNFLGDHW | 23 | OK | -34.7 | 0.4 | |
| 24 | PRMGWEKPE | 24 | OK | -34.1 | 0.4 | |
| 25 | WICVWHHAS | 25 | OK | -33.9 | 0.3 | |
| 26 | IRWCVDARY | 26 | OK | -30.0 | 0.6 | |
| 27 | WNAMSFCCS | 27 | OK | -28.9 | 0.4 | |
| 28 | IFHIMTEMW | 28 | OK | -28.7 | 0.2 | |
| 29 | FDRPRYRTT | 29 | OK | -28.6 | 0.4 | |
| 30 | QIEDMPTSK | 30 | OK | -28.3 | 0.4 | |
| 31 | FDCMMDMTK | 31 | OK | -28.0 | 0.3 | |
| 32 | NTVALKLRD | 32 | OK | -27.8 | 0.4 | |
| 33 | YHYHMLMQS | 33 | OK | -27.7 | 0.3 | |
| 34 | NITHNVWHR | 34 | OK | -27.6 | 0.3 | |
| 35 | DRNLEVEQI | 35 | OK | -26.7 | 0.3 | |
| 36 | HYNKWKHQE | 36 | OK | -25.6 | 0.4 | |
| 37 | ICMPPNTKN | 37 | OK | -24.6 | 0.3 | |
| 38 | SMIPVQEAS | 38 | OK | -24.5 | 0.3 | |
| 39 | YQRNELEYL | 39 | OK | -24.4 | 0.2 | |
| 40 | HYFDMLHFH | 40 | OK | -21.0 | 0.4 | |
| 41 | SHYFKHSNF | 41 | OK | -19.8 | 0.4 | |
| 42 | FIKQMEEST | 42 | OK | -18.5 | 0.3 | |
| 43 | KYQWMHYTP | 43 | OK | -16.9 | 0.6 | |
| 44 | FVGMRWKFL | 61 | Unbound | / | / | |
| 45 | WQIPDHRDH | 62 | Unbound | / | / | |
| 46 | QCFHPSFED | 63 | Unbound | / | / | |
| 47 | VPSSAKNRD | 64 | Unbound | / | / | |
| 48 | KHMTKCEQW | 65 | Unbound | / | / | |
| 49 | ETYQFRPNK | 66 | Unbound | / | / | |
| 50 | WNCHRDRPK | 67 | Unbound | / | / | |
| 51 | KHMTKCEQW | 68 | Unbound | / | / | |
| 52 | KCVVFHYDP | 69 | Unbound | / | / | |
| 53 | PTFEEFAAF | 70 | Unbound | / | / | |
| 54 | QCFHPSFED | 71 | Unbound | / | / | |
| 55 | EWLYRQEYH | 72 | Unbound | / | / | |
| 56 | QDYAPRASN | 73 | Unbound | / | / | |
| 57 | KDKAFKNVS | 74 | Unbound | / | / | |

Std. Error = Standard Error of Mean

Snapshots from the corresponding trajectories were extracted to compute the binding energy ΔG with MM-GBSA, a computational method already applied in similar studies with positive results (Lammi C, Zanoni C, Aiello G, Arnoldi A, & Grazioso G (2016) Lupin Peptides Modulate the Protein-Protein Interaction of PCSK9 with the Low Density Lipoprotein Receptor in HepG2 Cells. *Sci Rep* 6:29931, Ylilauri M & Pentikainen O T (2013) MMGBSA as a tool to understand the binding affinities of filamin-peptide interactions. *J Chem Inf Model* 53(10):2626-2633). 500 snapshots, selected in the more stable part of the simulation were used in the MM-GBSA calculations. Water molecules and counter-ions were stripped, while the protein and the peptide were parametrized using the same force field as in MD simulations. The polar contribution to solvation energy was computed with the Onufriev, Bashford and Case model setting the dielectric constant to 1 for the solute and 80 for the solvent (Onufriev A, Bashford D, & Case D A (2004) Exploring protein native states and large—scale conformational changes with a modified generalized born model. *Proteins* 55(2):383-394).

Based on the obtained MM-GBSA score, the 13 peptides with the best free energy ΔG were selected and tested experimentally in vitro. Table 3 below shows the sequences and the free energy ΔG of the 13 selected peptides:

TABLE 3

List of binding peptides ranked according to their theoretical binging free energy ΔG.

| Peptide Name | Sequence | SEQ ID NO. | $\Delta G_{GB} \pm SE$ |
|---|---|---|---|
| HBP01 | HEMYWEDEW | 5 | -52.78 ± 0.29 |
| HBP02 | IDLRFFMRQ | 6 | -52.00 ± 0.30 |
| HBP03 | FAFELIQTD | 7 | -51.72 ± 0.35 |
| HBP04 | CIPMMMHAW | 8 | -49.98 ± 0.27 |
| HBP05 | WISNWILMW | 3 | -45.84 ± 0.28 |
| HBP06 | TWNIHFADH | 9 | -45.57 ± 0.45 |
| HBP07 | HWTLANWCR | 2 | -45.20 ± 0.42 |
| HBP08 | GYHYERWIH | 1 | -45.09 ± 0.45 |
| HBP09 | QFMKNCEEM | 10 | -44.77 ± 0.40 |
| HBP10 | SINWHMYVN | 11 | -44.75 ± 0.31 |
| HBP11 | MYRENQPTR | 12 | -42.90 ± 0.43 |
| HBP12 | YHICWYGDY | 4 | -42.50 ± 0.48 |
| HBP13 | WLWYEWGWQ | 13 | -41.89 ± 0.30 |

FIG. 4 shows in panels A-M representations of the docking structures between BoxA of HMGB1 and the 13 peptides selected for in vitro testing.

Example 2: In Vitro Inhibition of CXCL12/HMGB1-Induced Activity

For in vitro testing, the 13 selected peptides as described above were synthesized. Synthetic peptides were custom-synthesized and HPLC-purified by GenScript (New Jersey, USA). Peptides were reconstituted with DMSO and stored at −20° C. HPLC-MS was used to confirm 98% or higher purity for each peptide.

The 13 identified and synthesized peptides were tested in in vitro chemotaxis, to assess their efficacy as inhibitors of the CXCL12/HMGB1-induced migration, on a murine cell line expressing the human CXCR4. To this end, a murine 300.19 PreB cell line stably transfected with the human CXCR4 was kept in culture in RPM1-1640, supplemented with 10% Fetal Bovine Serum, 1× non-essential amino acids, 1 mM Sodium pyruvate, 20 mM GlutaMAX, 50 μM 3-Mercaptoethanol, 50 U/ml Penicillin and 50 μg/ml Streptomycin (GIBCO).

Chemotaxis was performed using Boyden chambers with 5 μm pore membranes, as previously described (Uguccioni M, D'Apuzzo M, Loetscher M, Dewald B, & Baggiolini M (1995) Actions of the chemotactic cytokines MCP-1, MCP-2, MCP-3, RANTES, MIP-1 alpha and MIP-1 beta on human monocytes. *Eur J mmunol* 25(1):64-68). Murine 300.19 PreB cells stably transfected with the human CXCR4 were allowed to migrate for 90 min at 37° C. in response to a sub-optimal CXCL12 concentration (1 nM), in the presence of HMGB1 (300 nM), as previously described (Schiraldi M, et al. (2012) HMGB1 promotes recruitment of inflammatory cells to damaged tissues by forming a complex with CXCL12 and signaling via CXCR4. *J Exp Med* 209 (3):551-563). Inhibition of the synergistic activity of the heterocomplex CXCL12/HMGB1 was obtained by incubating CXCL12 and HMGB1 with 200 μM glycyrrhizin, as positive control (Schiraldi M, et al. (2012) HMGB1 promotes recruitment of inflammatory cells to damaged tissues by forming a complex with CXCL12 and signaling via CXCR4. *J Exp Med* 209(3):551-563). All peptides, at 100 μM, were incubated with CXCL12 and HMGB1 before assessing chemotaxis, to evaluate their ability to interfere with the heterocomplex formation, and inhibit the synergistic effect of HMGB1.

Figure 5:
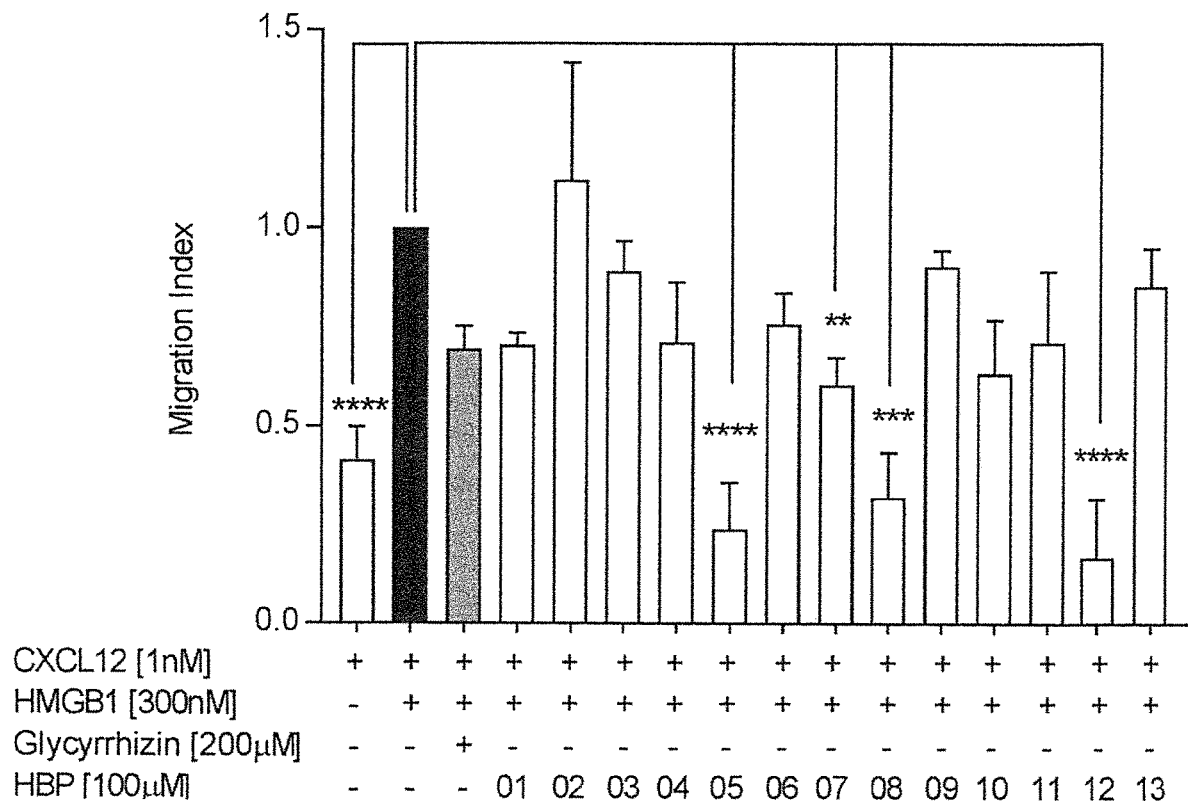
FIG. 5 shows for Example 2 the in vitro activity of the identified peptides. Inhibition of cell migration in response to the CXCL12/HMGB1 heterocomplex was assessed on 300-19 Pre-B cells transfected with human CXCR4 using the identified peptides or glycyrrhizin. Migration index was calculated as the ratio between the number of cells migrated in response to the heterocomplex in the presence or absence of the peptides. Migrated cells were counted in 5 high-power fields (HPF), and data are shown as mean±SEM of at least three independent experiments performed. *$p<0.05$; $p<0.01$; *$p<0.001$; ****$p<0.0001$.

Results are shown in FIG. 5. In general, the data confirm that compared to migration induced by CXCL12 alone, migration induced by the CXCL12/HMGB1 heterocomplex is enhanced (Schiraldi M, et al. (2012) HMGB1 promotes recruitment of inflammatory cells to damaged tissues by forming a complex with CXCL12 and signaling via CXCR4. *J Exp Med* 209(3):551-563). At 100 μM the peptides HBP05, HBP07, HBP08, and HBP12 inhibit the enhanced migration induced by the CXCL12/HMGB1 heterocomplex more than glycyrrhizin at 200 μM. Accordingly, HBP05 (SEQ ID NO: 3), HBP07 (SEQ ID NO: 2), HBP08 (SEQ ID NO: 1), and HBP12 (SEQ ID NO: 4) were selected for further testing.

Example 3: In Vitro Inhibition of CXCL12

Further experiments were performed with CXCL12 alone to identify peptides affecting cell migration induced by CXCL12 alone. To this end, experiments were performed in a similar manner as described in Example 2. Accordingly, murine 300.19 PreB cells stably transfected with human CXCR4 were used as described in Example 2.

Briefly, chemotaxis was performed using Boyden chambers with 5 μm pore membranes. Murine 300.19 PreB cells stably transfected with the human CXCR4 were allowed to migrate for 90 min at 37° C. in response to a sub-optimal CXCL12 concentration (1 nM). 200 μM glycyrrhizin were used as positive control. The control or peptides HBP05, HBP07, HBP08, and HBP12 (at 100 μM) were incubated with CXCL12 before assessing chemotaxis to evaluate their ability to interfere with CXCL12-induced cell migration.

Figure 6:
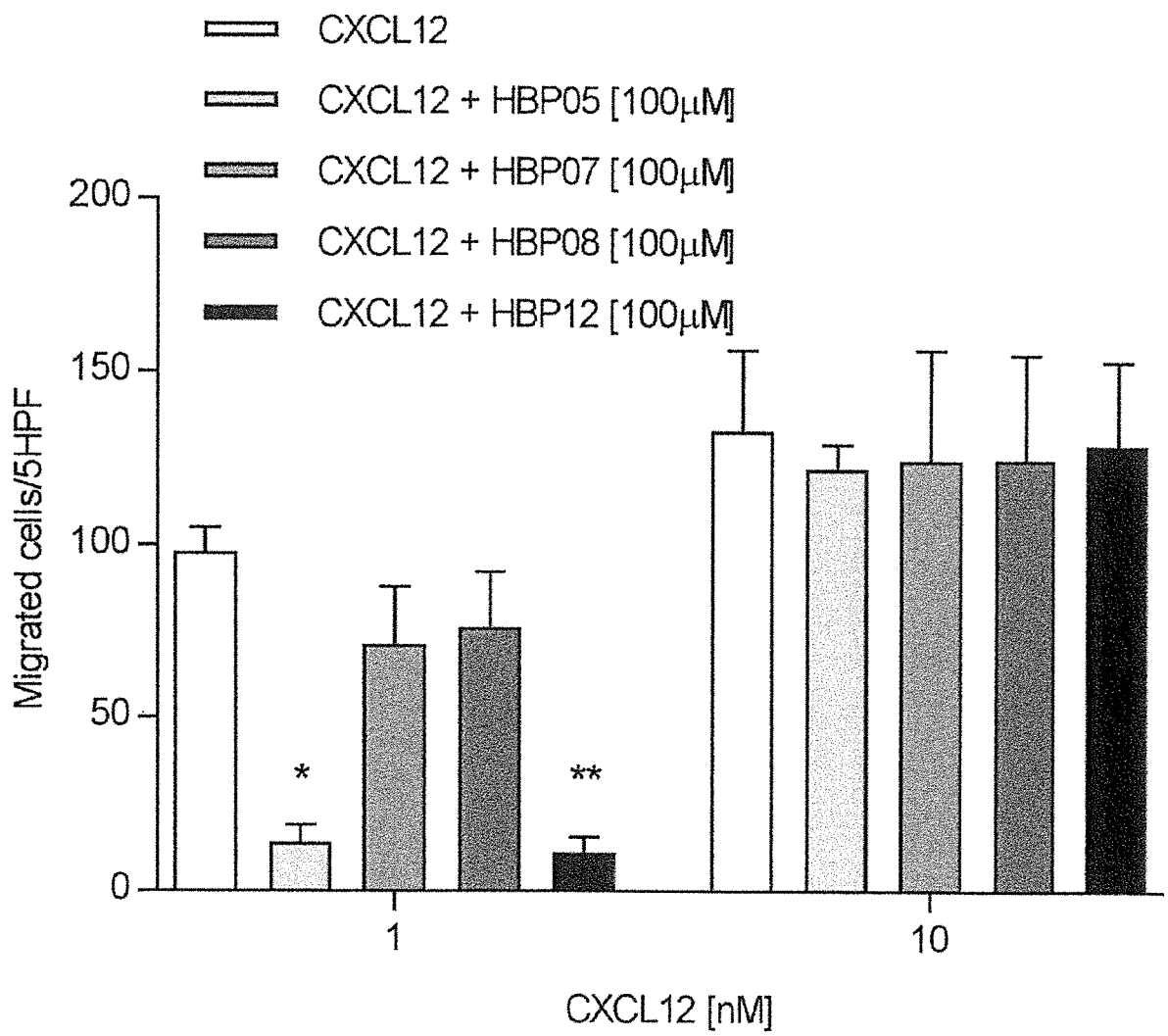
FIG. 6 shows for Example 3 the migration induced by CXCL12 alone in the presence or absence of the peptides identified in Example 2 as inhibitors of the migration induced by the CXCL12/HMGB1 heterocomplex. Migrated cells were counted in 5 high-power fields (HPF), and data are shown as mean±SEM of at least three independent experiments performed. *$p<0.05$; $p<0.01$; *$p<0.001$; ****$p<0.0001$.

Results are shown in FIG. 6. The data show that HBP07 and HBP08 do not affect CXCL12-induced cell migration, while HBP05 and HBP12 inhibit the migration induced by the chemokine alone (FIG. 6). In view thereof, HBP07 (SEQ ID NO: 2) and HBP08 (SEQ ID NO: 1) were selected for further experiments.

Example 4: In Vitro Inhibition of CXCL12/HMGB1-Induced Synergism in Human Cells

HBP07 (SEQ ID NO: 2) and HBP08 (SEQ ID NO: 1) were then tested on primary human monocytes. To this end, experiments were performed in a similar manner as described in Examples 2 and 3, wherein primary human monocytes were used instead of murine cells.

Human monocytes were freshly isolated from buffy-coats obtained from spontaneous donation from healthy individuals (Schweizerisches Rotes Kreuz, Basel), using positive selection with CD14 microbeads (Miltenyi Biotec), as previously described (Schiraldi M, et al. (2012) HMGB1 promotes recruitment of inflammatory cells to damaged tissues by forming a complex with CXCL12 and signaling via CXCR4. *J Exp Med* 209(3):551-563).

Briefly, chemotaxis was performed using Boyden chambers with 5 μm pore membranes, as described above. Freshly isolated human monocytes were allowed to migrate for 90 min at 37° C. in response to a sub-optimal CXCL12 concentration (1 nM), in the presence of HMGB1 (300 nM), as described above. Inhibition of the synergistic activity of the heterocomplex CXCL12/HMGB1 was obtained by incubating CXCL12 and HMGB1 with 200 μM glycyrrhizin, as positive control. Peptides HBP07 and HBP08, at 100 μM, were incubated with CXCL12 and HMGB1 before assessing chemotaxis, to evaluate their ability to interfere with the heterocomplex formation, and inhibit the synergistic effect of HMGB1.

In a further experiment, CXCL12-induced cell migration was assessed, similar to Example 3, but using human monocytes as described above. Briefly, chemotaxis was performed using Boyden chambers with 5 μm pore membranes. Freshly isolated human monocytes were allowed to migrate for 90 min at 37° C. in response to a sub-optimal CXCL12 concentration (1 nM). 200 μM glycyrrhizin were used as positive control. The control or peptides HBP07 and HBP08 (at 100 μM) were incubated with CXCL12 before assessing chemotaxis to evaluate their ability to interfere with CXCL12-induced cell migration.

Figure 7A:
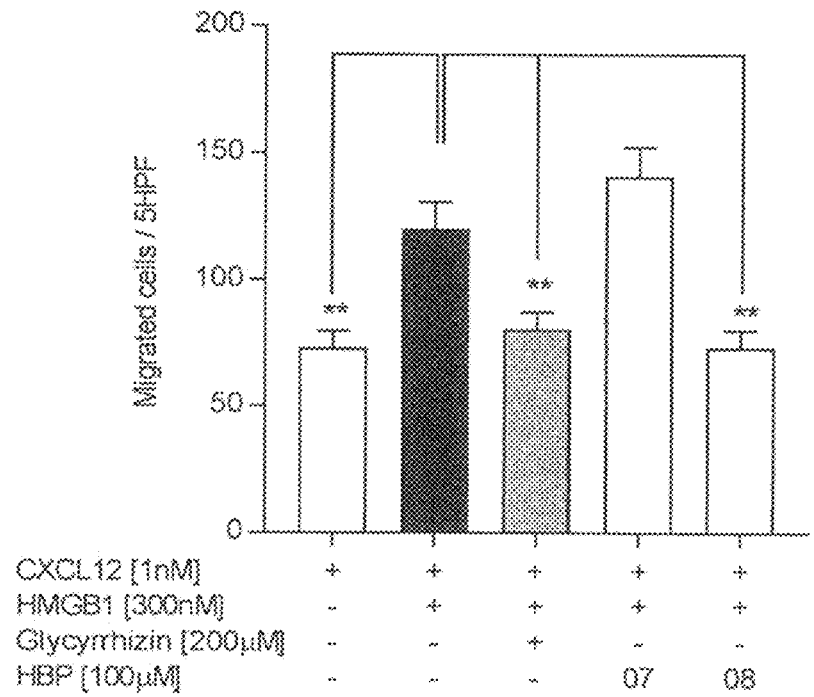
FIG. 7A-7B shows for Example 4 the inhibition of cell migration in response to the CXCL12/HMGB1 heterocomplex, assessed on human monocytes using HBP07, HBP08, or glycyrrhizin (FIG. 7A). Moreover, migration induced by CXCL12 alone in the presence or absence of HBP07 or HBP08 is shown (FIG. 7B). Migrated cells were counted in 5 high-power fields (HPF), and data are shown as mean±SEM of at least three independent experiments performed. *$p<0.05$; $p<0.01$; *$p<0.001$; ****$p<0.0001$.
Figure 7B:
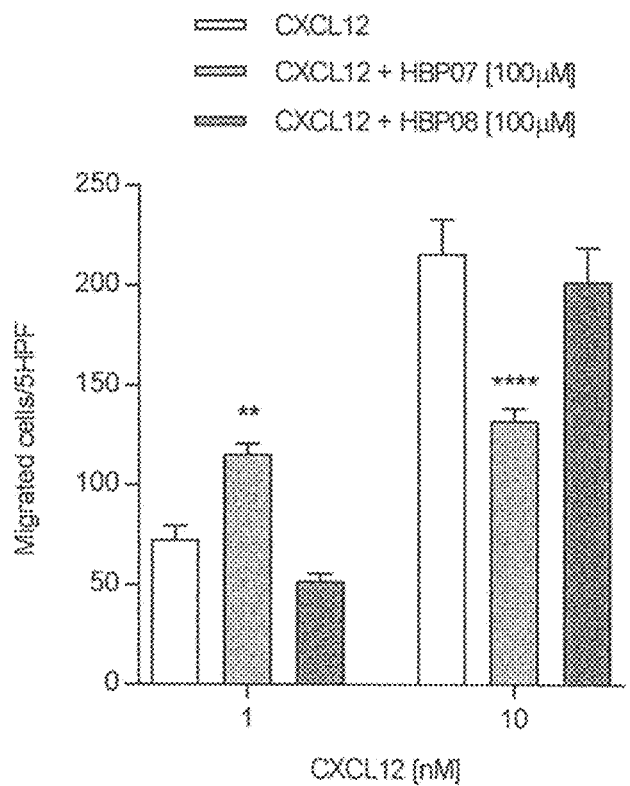

Results are shown in FIG. 7. Only peptide HBP08 (SEQ ID NO: 1) significantly blocked the activity of the heterocomplex (FIG. 7A), without altering the migration induced by CXCL12 alone (FIG. 7B).

In addition, toxicity of HBP08 was tested. Toxicity was assessed in the murine 300.19 PreB cell line expressing the human CXCR4, and on human monocytes. Cells were incubated for 2 h in the presence of HBP08 at 100 μM, stained by AnnexinVFITC/Propidium Iodide, and cell viability was analyzed by flow cytometry in comparison to the untreated control, following manufacturer's instructions. HBP08 exhibited no toxicity on both cell types.

Example 5: Affinity of HBP08 to HMGB1

To determine the affinity of HBP08 to HMGB1, the binding affinity ($K_d$) between HMGB1 and the HBP08 peptide was measured by microscale thermophoresis (MST) (Jerabek-Willemsen M, Wienken C J, Braun D, Baaske P, & Duhr S (2011) Molecular interaction studies using microscale thermophoresis. *Assay Drug Dev Technol* 9(4): 342-353).

Briefly, histidine tagged HMGB1 was labeled by the his-tag specific NT-647 dye (Monolith NTTM Protein Labelling Kit RED-NHS, NanoTemper® Technologies GmbH, Munich, Germany), for 30 minutes at room temperature. A fixed concentration of labeled HMGB1 (20 nM) was mixed with 16 1:1 serial dilutions of the HBP08 peptide (range 5 mM-0.15 nM). The protein and the peptide were incubated for 15 minutes at room temperature, to allow binding. MST analysis was performed using premium-coated capillary tubes on a NanoTemper® instrument using the following experimental settings: LED power of 5% (for fluorescence excitation), and laser power 40% (to create temperature gradient). $K_d$ values were calculate from compound concentration-dependent changes in normalized fluorescence (Fnorm). Independent experiments were performed to calculate the Kd value. Data were analyzed by the NanoTemper® analysis software.

Figure 8:
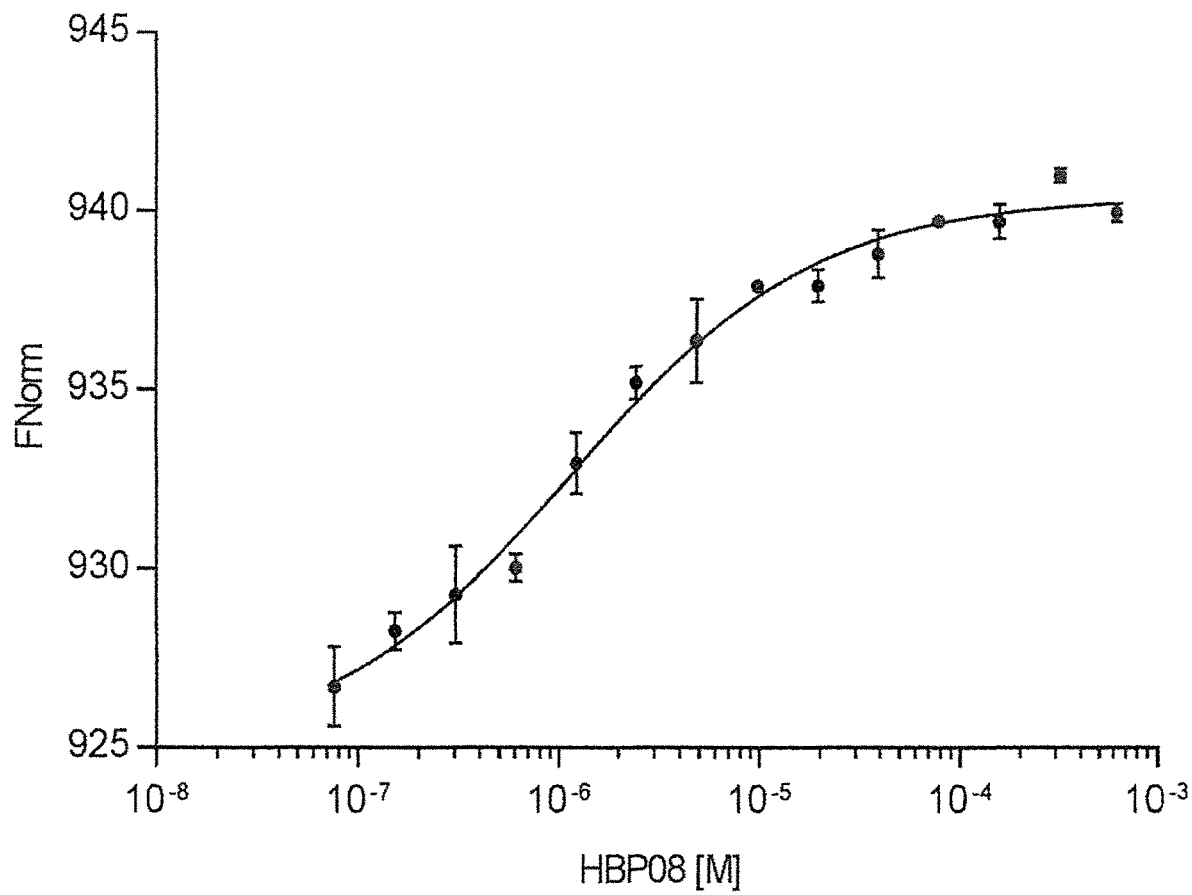
FIG. 8 shows for Example 5 the analysis by microscale thermophoresis of the interaction between HBP08 and HMGB1 (Kd=0.79±0.06 µM).

Results are shown in FIG. 8. A $K_d$ value of 0.79±0.06 μM was obtained. The affinity of the identified peptide is therefore two orders of magnitude higher than the one reported for glycyrrhizin ($K_d$=125 μM) (Mollica L, et al. (2007) Glycyrrhizin binds to high-mobility group box 1 protein and inhibits its cytokine activities. *Chem Biol* 14(4):431-441).

Overall, these results indicate HBP08 (SEQ ID NO: 1) as the first selective and potent peptide inhibitor of the CXCL12/HMGB1 heterocomplex, developed so far.

Example 6: Determination of Amino Acid Residues of HBP08 Involved in HMGB1 Binding To further characterize the interaction between HBP08 and HMGB1, the role of the nine amino acid residues in the binding of HBP08 to HMGB1 was determined using an alanine screening. Nine HBP08 mutant peptides were generated, wherein in each mutant one of the amino acid residues of HBP08 was substituted by alanine.

To this end, experimental alanine screening of the peptide HBP08 was performed by measuring the binding affinities of the HBP08 mutants to HMGB1 by MST. Furthermore, also the binding affinity of two additional peptides formed by the first (pentapept-1) or the last (pentapept-2) five residues of HBP08 was tested in these experiments.

Briefly, histidine tagged HMGB1 was labeled by the his-tag specific NT-647 dye (Monolith NTTM Protein Labelling Kit RED-NHS, NanoTemper® Technologies GmbH, Munich, Germany), for 30 minutes at room temperature. A solution with a concentration of 1 mM of the peptide to test has been prepared as first point and the other 15 points prepared by serial dilutions. After the addition of the protein the highest concentration of the peptide in the MST experiments has been 500 μM.

MST analysis was performed using premium-coated capillary tubes on a NanoTemper instrument using the following experimental settings: LED power of 5% (for fluorescence excitation), and laser power 40% (to create temperature gradient). Kd values were calculated from compound concentration-dependent changes in normalized fluorescence (Fnorm). Independent experiments were performed to calculate the Kd value. Data were analyzed by the NanoTemper analysis software.

In addition, computational alanine screening of the peptide HBP08 was performed by estimating the change in free energy (ΔΔG) by the computational procedure implemented in Bioluminate (Schrödinger Release 2018-4: BioLuminate, Schrödinger, LLC, New York, NY, 2018) (Beard, H., Cholleti, A., Pearlman, D., Sherman, W. & Loving, K. A. Applying Physics-Based Scoring to Calculate Free Energies of Binding for Single Amino Acid Mutations in Protein-Protein Complexes. *PLOS ONE* 8, e82849 (2013)).

For computational analysis, the difference in affinity between the mutate peptides and HMGB1 was calculated by the residue scanning functionality of Bioluminate. Starting from the HBP08 pose obtained by docking all residues were mutated, one at the time, to alanine. The structure of the complex between the mutated HPB08 and HMGB1 was then refined by the side-chain prediction and backbone minimization procedure. Finally, the change in the binding free energy (AG) has been estimated by the Prime MM-GBSA procedure (OPLS2005 force field and VSGB2.1 solvent model; Banks, J. L. et al. Integrated Modeling Program, Applied Chemical Theory (IMPACT). *J Comput Chem* 26, 1752-80 (2005)).

The results of the binding affinity measurements by MST (Kd) and the computational estimation of the predicted binding energy (ΔG) are shown in Table 4.

TABLE 4

Equilibrium dissociation constant (Kd) and predicted binding energy (ΔG) for the complexes between HMGB1 and the peptides tested.

| Peptide name | Peptide sequence | SEQ ID NO. | Kd (μM) | Predicted ΔG [kcal/mol] |
|---|---|---|---|---|
| HBP08 | GYHYERWIH | 1 | 0.8 ± 0.06 | |
| HBP08-A1 | AYHYERWIH | 45 | 8.5 ± 3.4 | -2.29 |
| HBP08-A2 | GAHYERWIH | 46 | 5.8 ± 1.1 | 3.26 |
| HBP08-A3 | GYAYERWIH | 47 | 26.2 ± 4.8 | 11.83 |
| HBP08-A4 | GYHAERWIH | 48 | 9.9 ± 1.3 | 0.14 |
| HBP08-A5 | GYHYARWIH | 49 | 0.8 ± 0.2 | 1.86 |
| HBP08-A6 | GYHYEAWIH | 50 | N.D.# | 11.03 |
| HBP08-A7 | GYHYERAIH | 51 | 21.9 ± 4.5 | 17.62 |
| HBP08-A8 | GYHYERWAH | 52 | 1.9 ± 0.6 | -0.02 |
| HBP08-A9 | GYHYERWIA | 53 | >100 | 4.23 |
| Pentapept-1 | GYHYE | 59 | No binding* | |
| Pentapept-2 | ERWIH | 58 | 200 ± 80 | |

*in the explored concentraton range no binding observed
N.D.# not determined because poorly soluble in PBS The comparison between the experimentally determined Kd and the predicted ΔG values shows a good qualitative and quantitative match. Moreover, all HBP08 mutants were found to bind to HMGB1.

Of the four HBP08 mutants, for which the most positive binding ΔΔG was predicted (HBP08-A3, HBP08-A6, HBP08-A7 and HBP08-A9), three mutant peptides (HBP08-A3, HBP08-A7 and HBP08-A9) showed decreased affinity for HMGB1. The fourth peptide of those mutants, HBP08-A6, in which an arginine residue is mutated in alanine, resulted in a poorly soluble peptide, whose affinity could not be determined by MST.

For the other five HPB-08 mutant peptides (HBP08-A1, HBP08-A2, HBP08-A4, HBP08-A5 and HBP08-A8) smaller binding ΔΔG were predicted and their Kd values were close to the value measured for HPB-08 (SEQ ID NO: 1).

Regarding the truncated HBP08 peptides pentapept-1 and pentapept-2, no binding was observed for pentapept-1 (in the same range of concentration as used in the analysis of the other peptides), while a Kd of 200±80 μM was determined for pentapept-2. This shows that the peptide formed by the last five residues of HBP08 is still able to bind (albeit with lower affinity) also in absence of the first four residues of HBP08, while no binding was observed for the peptide formed by the first five residues of HBP08 (without the last four residues).

In summary, both computational and experimental analysis of the binding determinants of HPB08 indicated that the residues at the positions 7 and 9 are the most important for the binding of HBP08 to HMGB1. In addition, also the amino acid residue at position 3 is assumed to influence the binding affinity.

Figure 9:
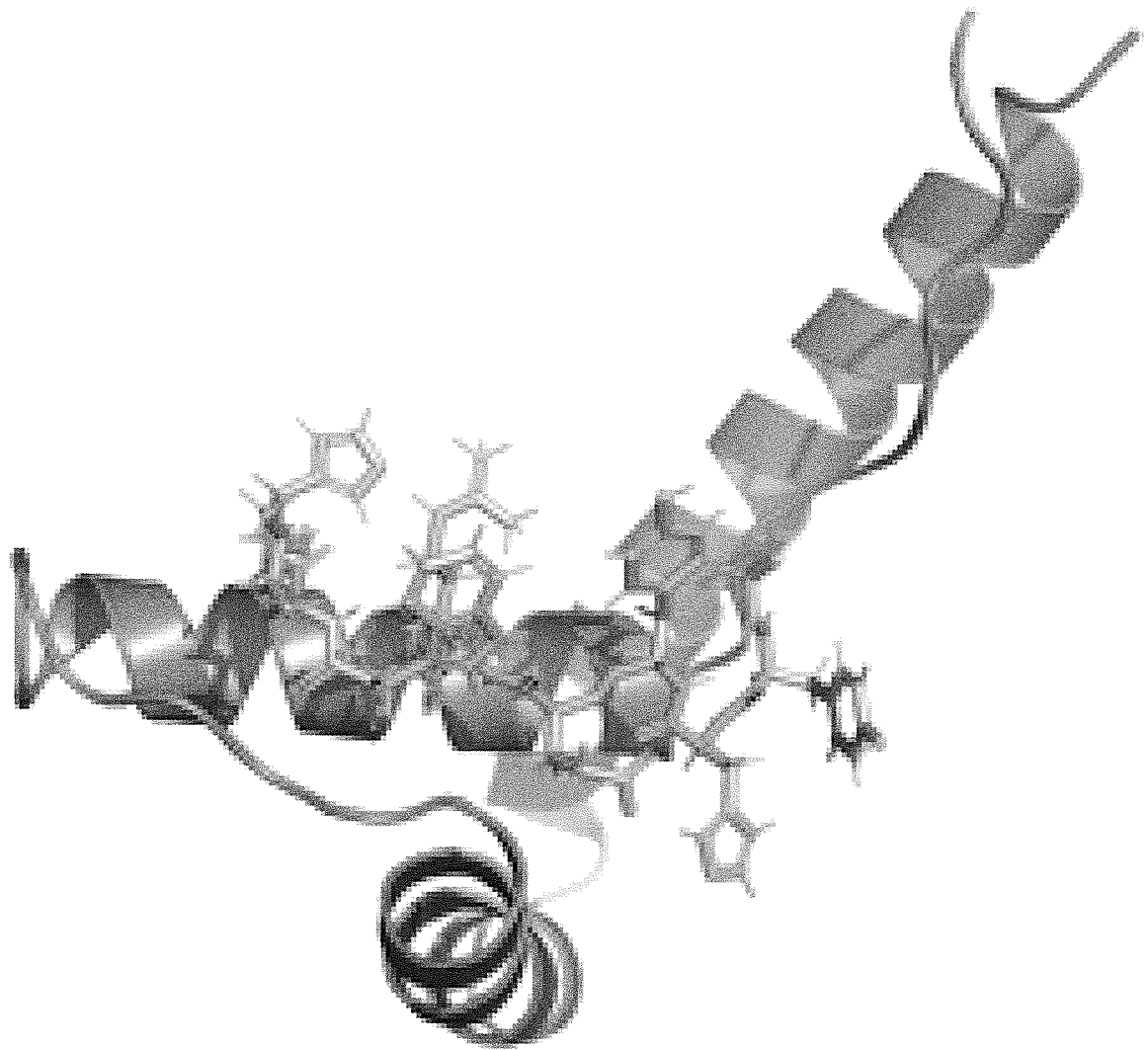
FIG. 9 shows peptide HBP08 bound to BoxA of HMGB1.

To further understand the individual contributions of these key residues at positions 3, 7 and 9 of HBP08, the 3D structure of HMGB1-HBP08 complex was analyzed by visual inspection of the protein structure aiming to identify key interactions such as H-bonds, charge-charge interactions, and hydrophobic contacts. FIG. 9 shows the peptide HBP08 (SEQ ID NO: 1) bound to BoxA of HMGB1.

The analysis revealed that both, HPB08-His9 and HPB08-Trp7, form H-bond interactions with Arg24 and Asp67 of HMGB1, respectively. HPB08-His3, in contrast, is placed in a cavity delimited by Ala17, Val20 and Arg24 of HMGB1? and, thus, its contribution to the binding of HBP08 to HMGB1 appears to be due to Van-der-Waals interactions.

In addition, the structure of the HPB08-BoxA complex was compared with that of the BoxA-CXCL12 complex obtained integrating previous NMR investigations (Schiraldi M, et al. (2012) HMGB1 promotes recruitment of inflammatory cells to damaged tissues by forming a complex with CXCL12 and signaling via CXCR4. *J Exp Med* 209(3):551-563) and computational modeling by evaluating if the contact surface between HMGB1 and CXCL12 was, at least in part, the same of the complex between HMGB1 and HPB08. A model of HBP08 bound to BoxA is shown in FIG. 10 A-C.

This analysis disclosed that the HBP-08 binding site on BoxA is formed by some residues of HMGB1, which are known to be important for the CXCL12 binding of HMGB1. This indicates that the peptide HBP08 can competitively antagonize the formation of the HMGB1/CXCL12 heterocomplex.

Example 7: Exemplary Sequence Variants of HBP08

Next, exemplary sequence variants of HBP08 were designed and their binding affinity to HMGB1 was experimentally measured by MST as described in Example 6. The results of the binding experiments are shown in Table 5.

TABLE 5

Equilibrium dissociation constant (Kd) for the complexes between HMGB1 and the peptides tested.

| Peptide name | Peptide sequence | SEQ ID NO. | Kd (μM) |
|---|---|---|---|
| HBP08-D2 | GDHYERWIH | 54 | 9.4 |
| HBP08-K9 | GYHYERWIK | 55 | 9.6 |
| HBP08-K2 | GKHYERWIH | 56 | 5.8 |
| XHBP08 | HYWYERWEH | 57 | 0.03 |

All tested HBP08 mutants showed a good binding affinity for HMGB1. In particular XHBP08 (SEQ ID NO: 57) showed a very good binding affinity for HMGB1, which is even improved in comparison to HBP08.

Example 8: Development of a D-Retro-Inverso Version of HBP08

L-peptides are susceptible to the action of proteolytic enzymes such as peptidases and are, therefore, not ideal for in vivo use. D-peptides are less prone to the action of peptidases and to the acidic hydrolysis that occurs in the stomach, which increases their oral bioavailability and blood circulation time (Feng Z, Xu B. Inspiration from the mirror: D-amino acid containing peptides in biomedical approaches. Biomol Concepts. 2016 Jun. 1; 7(3):179-87). Furthermore D-peptides have a lower immunogenicity. Taken together, these features make D-peptides very interesting from a drug development point of view.

To exploit the potential of this strategy in a drug development perspective, a D-retro-inverso version (Guichard G, Benkirane N, Zeder-Lutz G, van Regenmortel M H, Briand J P, Muller S (1994). Antigenic mimicry of natural L-peptides with retro-inverso-peptidomimetics. Proceedings of the National Academy of Sciences. 91 (21): 9765-9769) of HBP08 was generated. D-retro-inverso peptide HBP08-RI is an all-D amino acid peptide (i.e., composed of D-amino acids only), wherein the order of the amino acid residues is reversed in comparison to HBP08.

Next, the binding affinity of HBP08-RI (SEQ ID NO: 44), the D-retro-inverso analogue of HBP08, to HMGB1 was experimentally measured by MST as described in Example 6. The results of the binding experiments indicated that HBP08-RI has a good affinity for HMGB1 (Kd=14.0±4.5 µM) and represents, therefore, a good candidate for future drug development studies.

TABLE OF SEQUENCES AND SEQ ID NUMBERS (SEQUENCE LISTING):

| SEQ ID NO | Sequence | Remarks |
| --- | --- | --- |
| SEQ ID NO: 1 | GYHYERWIH | HBP08 |
| SEQ ID NO: 2 | HWTLANWCR | HBP07 |
| SEQ ID NO: 3 | WISNWILMW | HBP05 |
| SEQ ID NO: 4 | YHICWYGDY | HBP12 |
| SEQ ID NO: 5 | HEMYWEDEW | HBP01 |
| SEQ ID NO: 6 | IDLRFFMRQ | HBP02 |
| SEQ ID NO: 7 | FAFELIQTD | HBP03 |
| SEQ ID NO: 8 | CIPMMMHAW | HBP04 |
| SEQ ID NO: 9 | TWNIHFADH | HBP06 |
| SEQ ID NO: 10 | QFMKNCEEM | HBP09 |
| SEQ ID NO: 11 | SINWHMYVN | HBP10 |
| SEQ ID NO: 12 | MYRENQPTR | HBP11 |
| SEQ ID NO: 13 | WLWYEWGWQ | HBP13 |
| SEQ ID NO: 14 | DYCWKIMTQ | peptide |
| SEQ ID NO: 15 | WCHFFFPHW | peptide |
| SEQ ID NO: 16 | MKSSDCCLE | peptide |
| SEQ ID NO: 17 | EWFVMKHLN | peptide |
| SEQ ID NO: 18 | MIRDQILHN | peptide |
| SEQ ID NO: 19 | WHQLTEHWI | peptide |
| SEQ ID NO: 20 | HDHDFWAWY | peptide |
| SEQ ID NO: 21 | WQWHQFQGR | peptide |
| SEQ ID NO: 22 | VMASWQHGL | peptide |
| SEQ ID NO: 23 | LDNFLGDHW | peptide |
| SEQ ID NO: 24 | PRMGWEKPE | peptide |
| SEQ ID NO: 25 | WICVWHHAS | peptide |
| SEQ ID NO: 26 | IRWCVDARY | peptide |
| SEQ ID NO: 27 | WNAMSFCCS | peptide |
| SEQ ID NO: 28 | IFHIMTEMW | peptide |
| SEQ ID NO: 29 | FDRPRYRTT | peptide |
| SEQ ID NO: 30 | QIEDMPTSK | peptide |

-continued

TABLE OF SEQUENCES AND SEQ ID NUMBERS (SEQUENCE LISTING):

| SEQ ID NO | Sequence | Remarks |
|---|---|---|
| SEQ ID NO: 31 | FDCMMDMTK | peptide |
| SEQ ID NO: 32 | NTVALKLRD | peptide |
| SEQ ID NO: 33 | YHYHMLMQS | peptide |
| SEQ ID NO: 34 | NITHNVWHR | peptide |
| SEQ ID NO: 35 | DRNLEVEQI | peptide |
| SEQ ID NO: 36 | HYNKWKHQE | peptide |
| SEQ ID NO: 37 | ICMPPNTKN | peptide |
| SEQ ID NO: 38 | SMIPVQEAS | peptide |
| SEQ ID NO: 39 | YQRNELEYL | peptide |
| SEQ ID NO: 40 | HYFDMLHFH | peptide |
| SEQ ID NO: 41 | SHYFKHSNF | peptide |
| SEQ ID NO: 42 | FIKQMEEST | peptide |
| SEQ ID NO: 43 | KYQWMHYTP | peptide |
| SEQ ID NO: 44 | HIWREYHYG | all D amino acids; HBP08-RI |
| SEQ ID NO: 45 | AYHYERWIH | HBP08-A1 |
| SEQ ID NO: 46 | GAHYERWIH | HBP08-A2 |
| SEQ ID NO: 47 | GYAYERWIH | HBP08-A3 |
| SEQ ID NO: 48 | GYHAERWIH | HBP08-A4 |
| SEQ ID NO: 49 | GYHYARWIH | HBP08-A5 |
| SEQ ID NO: 50 | GYHYEAWIH | HBP08-A6 |
| SEQ ID NO: 51 | GYHYERAIH | HBP08-A7 |
| SEQ ID NO: 52 | GYHYERWAH | HBP08-A8 |
| SEQ ID NO: 53 | GYHYERWIA | HBP08-A9 |
| SEQ ID NO: 54 | GDHYERWIH | HBP08-D2 |
| SEQ ID NO: 55 | GYHYERWIK | HBP08-K9 |
| SEQ ID NO: 56 | GKHYERWIH | HBP08-K2 |
| SEQ ID NO: 57 | HYWYERWEH | XHBP08 |
| SEQ ID NO: 58 | ERWIH | Pentapept-2 |
| SEQ ID NO: 59 | GYHYE | Pentapept-1 |
| SEQ ID NO: 60 | MGKGDPKKPRGKMSSYAFFVQTCREEHKKK HPDASVNFSEFSKKCSERWKTMSAKEKGKF EDMAKADKARYEREMKTYIPPKGETKKKFKD PNAPKRPPSAFFLFCSEYRPKIKGEHRGLSIG DVAKKLGEMWNNTAADDKQPYEKKAAKLKE KYEKDIAAYRAKGKPDAAKKGVVKAEKSKKK KEEEEDEEDEEDEEEEEDEEDEDEEEDDDDE | HMGB1 |
| SEQ ID NO: 61 | FVGMRWKFL | peptide |
| SEQ ID NO: 62 | WQIPDHRDH | peptide |
| SEQ ID NO: 63 | QCFHPSFED | peptide |
| SEQ ID NO: 64 | VPSSAKNRD | peptide |

-continued

| SEQ ID NO | Sequence | Remarks |
|---|---|---|
| SEQ ID NO: 65 | KHMTKCEQW | peptide |
| SEQ ID NO: 66 | ETYQFRPNK | peptide |
| SEQ ID NO: 67 | WNCHRDRPK | peptide |
| SEQ ID NO: 68 | KHMTKCEQW | peptide |
| SEQ ID NO: 69 | KCVVFHYDP | peptide |
| SEQ ID NO: 70 | PTFEEFAAF | peptide |
| SEQ ID NO: 71 | QCFHPSFED | peptide |
| SEQ ID NO: 72 | EWLYRQEYH | peptide |
| SEQ ID NO: 73 | QDYAPRASN | peptide |
| SEQ ID NO: 74 | KDKAFKNVS | peptide |

The invention claimed is:

1. A peptide comprising: (i) the amino acid sequence that is at least 75% identical to any one selected from the group consisting of SEQ ID NOs: 1-57, wherein the peptide is no more than 12 amino acids in length; or (ii) the amino acid sequence that is at least 75% identical to SEQ ID NO: 58, wherein the peptide is no more than 6 amino acids in length; and wherein the peptide comprising (i) or (ii) is modified at its N-terminus by an $NH_2$-protection group, and/or its C-terminus by an amide modification.

2. The peptide according to claim 1, wherein the peptide comprises the amino acid sequence that is at least 88% identical to any one selected from the group consisting of SEQ ID NOs: 1-57.

3. The peptide according to claim 1, wherein the peptide comprises the amino acid sequence that is at least 75% identical to any one selected from the group consisting of SEQ ID NOs: 1-13, 44 and 57.

4. The peptide according to claim 1, wherein the peptide comprises the amino acid sequence that is at least 75% identical to SEQ ID NO: 1, and wherein Trp7 and His9 in SEQ ID NO: 1 are maintained.

5. The peptide according to claim 1, wherein the peptide comprises the amino acid sequence of SEQ ID NO: 1.

6. The peptide according to claim 1, wherein the peptide comprises the amino acid sequence that is at least 75% identical to SEQ ID NO: 44, wherein the amine acids are D-amino acids, and wherein D-His1 and D-Trp3 in SEQ ID NO: 44 are maintained.

7. The peptide according to claim 1, wherein the peptide comprises the amino acid sequence of SEQ ID NO: 44, and wherein the amino acids are D-amino acids.

8. The peptide according to claim 1, wherein the peptide comprises the amino acid sequence that is at least 75% identical to SEQ ID NO: 57, and wherein Trp7 and His9 in SEQ ID NO: 57 are maintained.

9. The peptide according to claim 1, wherein the peptide comprises the amino acid sequence of SEQ ID NO: 57.

10. A composition comprising the peptide according to claim 1, and optionally a carrier, diluent and/or excipient.

11. A peptide consisting of the amino acid sequence selected from the group consisting of SEQ ID NOs: 1-58.

12. The peptide according to claim 11, wherein the peptide binds to BoxA of high-mobility-group-protein 1 (HMGB1).

13. The peptide according to claim 12, wherein the $K_d$ value for binding of the peptide to HMGB1 is less than 100 µM.

14. The peptide according to claim 11, wherein the peptide inhibits C-X-C motif chemokine ligand 12 (CXCL12)/HMGB1 interaction.

15. A composition comprising the protein of claim 11, and optionally a carrier, diluent and/or excipient.

16. A method of treating inflammation in a subject in need thereof, wherein the method comprises administering to the subject a therapeutically effective amount of a peptide according to claim 11, and optionally a carrier, diluent and/or excipient.

17. A method of treating inflammation in a subject in need thereof, wherein the method comprises administering to the subject a therapeutically effective amount of a composition comprising a peptide according to claim 11, and a carrier, diluent and/or excipient.

18. A protein comprising the amino acid sequence selected from the group consisting of SEQ ID NOs: 1-57.

19. A method of treating inflammation in a subject in need thereof, wherein the method comprises administering to the subject in need thereof a therapeutically effective amount of a protein according to claim 15, and optionally a carrier, diluent and/or excipient.

20. A method of treating inflammation in a subject in need thereof, wherein the method comprises administering to the subject a therapeutically effective amount of a protein according to claim 18, and a carrier, diluent and/or excipient.

21. A method of treating inflammation in a subject in need thereof, wherein the method comprises administering to the subject a therapeutically effective amount of a composition comprising a protein according to claim 18, and a carrier, diluent and/or excipient.

* * * * *